(12) United States Patent
Adamczyk et al.

(10) Patent No.: US 6,797,479 B2
(45) Date of Patent: Sep. 28, 2004

(54) REAGENTS AND METHODS FOR THE DETECTION AND QUANTIFICATION OF VANCOMYCIN IN BIOLOGICAL FLUIDS

(75) Inventors: Maciej Adamczyk, Gurnee, IL (US); Elaine M. Brate, Grayslake, IL (US); Mary M. Perkowitz, Lake Zurich, IL (US); Sushil D. Rege, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/174,121

(22) Filed: Oct. 16, 1998

(65) Prior Publication Data

US 2002/0009708 A1 Jan. 24, 2002

Related U.S. Application Data

(63) Continuation-in-part of application No. 09/026,869, filed on Feb. 20, 1998, now abandoned, which is a continuation of application No. 08/416,567, filed on Apr. 4, 1995, now abandoned.

(51) Int. Cl.[7] .......................... C12Q 1/00; G01N 33/53; C12P 21/08
(52) U.S. Cl. ............................. 435/7.1; 435/4; 435/7.9; 435/7.92; 436/518; 530/387.1; 530/388.9; 530/389.1; 549/223
(58) Field of Search ............................. 435/4, 7.1, 7.9, 435/7.92, 7.93, 7.95, 345, 971, 975, 961, 967–968; 436/518, 517, 543, 546, 547, 548, 815, 805, 822, 823, 8, 172, 800; 530/387.1, 388.9, 388.1, 389.1, 389.8, 802, 808; 549/223

(56) References Cited

U.S. PATENT DOCUMENTS

| | | | |
|---|---|---|---|
| 4,420,568 A | | 12/1983 | Wang et al. |
| 4,668,640 A | | 5/1987 | Wang et al. |
| 4,670,258 A | * | 6/1987 | Harris et al. ............... 424/115 |
| 5,359,093 A | * | 10/1994 | Adamczyk et al. ......... 549/223 |
| 5,747,352 A | | 5/1998 | Yan et al. ................... 436/533 |

FOREIGN PATENT DOCUMENTS

| | | |
|---|---|---|
| EP | 0221282 | 3/1987 |
| WO | 9532428 | 11/1995 |
| WO | 9631780 | 10/1996 |

OTHER PUBLICATIONS

Database Biosis 'Online! Biosciences Information Service, Philadelphia, PA, Anne et al.: "Potential Problem with Fluorescence Polarization Immunoassay Cross–Reactivity to Vancomycin Degradation Product CDP–1 Its Detection in Sera of Renally Impaired Patients" retrieved from STN XP002132079 Abstract & Ther Drug Monit, (1989) 11 (5), 585–591.
Pfaller et al., *Journal of Clinical Microbiology*, 20 (3): 311–316 (1984).
Schwenzer et al., *Therapeutic Drug Monitoring*, 5 (3): 341–345 (1983).
Wang et al., *Journal of Pharmaceutical & Biomedical Analysis*, 11 (10): 871–879 (1993).
Sundram et al., *Journal of Organic Chemistry*, 60: 1102–1103 (1995).
Hu et al., *Therapeutic Drug Monitoring*, 12: 562–569 (1990).
Crossley et al., *Antimicrobial Agents and Chemotherapy*, 17 (4): 654–657 (1980).
Jolley et al., *Clinical Chemistry*, 27 (7): 341–345 (1981).
EMIT Vancomycin Assay Product Insert, 8W584UL.4, Syva Company, 1988.

\* cited by examiner

*Primary Examiner*—Padmashri Ponnaluri
(74) *Attorney, Agent, or Firm*—Regina M. Anderson

(57) ABSTRACT

Immunoassay reagents, methods and test kits for the specific quantification of vancomycin in a test sample are disclosed. The reagent comprises antibodies prepared with immunogens of FIG. 6 wherein P is an immunogenic carrier material and X is a linking moiety. Also described is the synthesis of labeled reagents of FIG. 8 wherein Q is a detectable moiety, preferably fluorescein or a fluorescein derivative, and X is a linking moiety.

9 Claims, 26 Drawing Sheets

VANCOMYCIN

CDP-I

CDP-II

Thyroglobulin
EDAC
Phosphate Buffer
pH 6.7

Vancomycin

DMF, WATER
pH 6

N-Vancosaminyl Derived Tracers

N-Methylleucyl Derived Tracers

Carboxyl-HDA Derived Tracers (2)

| Compound | R₁ | R₂ | R₃ | R₄ |
|---|---|---|---|---|
| *Vancomycin Analogs* | | | | |
| (1) | [disaccharide with NH₂] | Cl | H | OH |
| (5) | [monosaccharide] | Cl | H | OH |
| (6) | H | Cl | H | OH |
| (7) | [disaccharide with NHAc] | Cl | H | OH |
| (8) | [disaccharide with NH₂] | H | H | OH |
| (9) | [disaccharide with NH₂] | Cl | H | $\text{-}\underset{H}{N}\text{-}(CH_2)_6\text{-}NH_2$ |
| *CDP Analogs* | | | | |
| (10) | [disaccharide with NH₂] | Cl | (-) | (-) |
| (11) | H | Cl | (-) | (-) |
| (12) | [monosaccharide] | H | (-) | (-) |

RED: SUGAR MOIETIES
BLUE: PEPTIDE BINDING REGION
GREEN: RING 2 CHLORINE

REAGENTS AND METHODS FOR THE DETECTION AND QUANTIFICATION OF VANCOMYCIN IN BIOLOGICAL FLUIDS

RELATED APPLICATION INFORMATION

This application is a continuation-in-part of U.S. Ser. No. 09/026,869 filed on Feb. 20, 1998, now abandoned which is a continuation of U.S. Ser. No. 08/416,567 filed on Apr. 4, 1995 now abandoned.

FIELD OF THE INVENTION

The present invention relates to the quantification of vancomycin in a test sample. In particular, the present invention relates to immunogens, antibodies prepared from such immunogens, and labeled reagents for the specific quantification of vancomycin in a test sample, preferably for use in fluorescence polarization immunoassays.

BACKGROUND OF THE INVENTION

For the past 30 years, vancomycin has been the drug of choice for the treatment of Gram-positive infections caused by methicillin resistant *Staphylococcus aureus*. It is also the treatment in bacterial infections in patients allergic to β-lactam antibiotics. Vancomycin is produced by *Amycolatopsis orientalis* (previously designed *Nocardia orientalis* and *Streptomyces orientalis*). Vancomycin is resistant to Gram-negative organisms. Cross resistance with other antibiotics is unknown and in spite of its long usage, there have been few reports of the emergence of resistant organisms during therapy. Vancomycin is not absorbed from the gastrointestinal tract, and hence the antibiotic is used to treat enterocolitis caused especially by *Clostridium difficile* in the gut. Nagarajan, R., J. *Antibiotics,* 46:1181 (1993). Vancomycin exerts its antibacterial action by binding preferentially to peptide intermediates involved in the biosynthesis of bacterial cell wall peptidoglycan.

Vancomycin is eliminated via the kidneys. The half life of the drug, 5–11 hours in normal patients, is extended to 2–5 days in patients with renal insufficiency, and is even longer in dialysis patients. While vancomycin is a relatively safe drug; adverse effects which have been observed include nephrotoxicity and autotoxicity.

For safe administration of vancomycin, it is customary to quantify its levels in patient blood. It has been suggested that because the drug stays longer in the body of a renally impaired patient, exposure to internal body temperature for longer periods results in the accumulation of degradation products which are known as Crystalline Degradation Products I and II (CDP-I and CDP-II). CDP-I and CDP-II are rotational isomers which can be separately isolated. Vancomycin and its two major degradation products CDP-I & CDP-II are shown in FIGS. 1–3, respectively.

It is known that vancomycin is unstable in an aqueous environment. U.S. Pat. No. 4,670,258 to Harris, et al. discloses a composition of vancomycin and a tripeptide which is said to stabilize the drug in an aqueous solution. However, such tripeptides can interfere with immunoassay techniques. For example, such interference may occur where an antibody competes with a stabilizing peptide for the same binding site of the analyte.

Historically, vancomycin concentrations in biological fluids have been determined by fluorescence immunoassay (FIA), high performance liquid chromatography (HPLC), radio immunoassay (RIA), the enzyme multiplied immunoassay technique (EMIT) or microbiological techniques. While HPLC is considered by those skilled in the art as the most accurate of all methods for quantification of vancomycin, it is a slow and labor intensive method which requires highly trained personnel and specialized equipment which is not always available in every clinical setting.

More recently, fluorescent polarization techniques have been used to assay for vancomycin. Fluorescent polarization techniques are based on competitive binding immunoassay principles. The principle behind fluorescent polarization is that a fluorescent labeled compound, when excited by a linearly polarized light, will emit fluorescence having a degree of polarization inversely proportional to its rate of rotation. Therefore, when a fluorescent labeled tracer-antibody complex is excited by a linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate produced in a competitive binding immunoassay.

Fluorescent polarization techniques and compounds suitable for use as fluorescent labels have been described in the art. For instance, U.S. Pat. Nos. 4,510,251 and 4,614,823, to Kirkemo et al., disclose fluorescent polarization assay for ligands using aminomethyl fluorescein derivatives, respectively. U.S. Pat. No. 4,476,229, to Fino et al., discloses substituted carboxyfluoresceins, including those containing a vancomycin analog, for use in fluorescence polarization immunoassay. U.S. Pat. Nos. 4,420,568 and 5,097,097 to Wang et al., disclose fluorescent polarization immunoassay utilizing substituted triazinylaminofluoresceins as tracers. Wang in U.S. Pat. No. 4,420,568 discloses reaction of vancomycin and dichlorotriazinylaminofluorescein (DTAF). However, this patent does not describe the structure of the product of such a reaction or its application in the heterogeneous system. Griffin et al., (JACS 115, 6482 (1993)) describe a selective method for the synthesis of vancomycin derivatives bearing alkyl, imidazole and amine functional groups attached to the C-terminus and indicated usefulness of this method for preparation of derivatives bearing different functional groups. However, there is no description of the synthesis of immunogenic material or immunocomponents and their use for quantification of vancomycin.

Commercially available fluorescent polarization assays (FPIA) for vancomycin are available. For instance, commercially available assays (Abbott TDX®, TDXFLX® assays, (hereinafter referred to as the "commercially available Abbott Vancomycin assays(s)")) include reagents for the quantitative measurement of vancomycin in serum or plasma samples. These assays use a vancomycin derivative labeled with a dichlorotriazinylaminofluorescein (DTAF) (hereinafter referred to as the "commercially available tracer"), and sheep polyclonal antibodies against vancomycin (hereinafter referred to as "commercially available antibodies").

FPIAs have an advantage over radioimmunoassays (RIA) in that there are no radioactive substances to dispose of and they are homogeneous assays that can be easily and rapidly performed. However, it has been reported that the commercially available vancomycin assays show an occasional increase in measured vancomycin values which do not conform with HPLC measurements. These increases have been attributed to increased cross-reactivity with CDP-I and CDP-II. As noted above, the isomers CDP-I and CDP-II can be separately isolated. As expected, any solution made from CDP-I will always contain an equilibrium mixture of both isomers. Thus, measures of CDP-I cross-reactivity reported herein measure the cross-reactivity of the equilibrium mixture.

Thus there exists a continuing need for improved assays which can quickly and accurately determine the concentration of vancomycin in the presence of cross-reactive degradation products in biological fluid. Accordingly, the present invention provides unique antibody reagents and labeled reagents for the quantification of vancomycin in a test sample. The invention also provides immunoassay methods which utilize these unique reagents. Also provided are synthetic procedures for preparing immunogens which are employed for the production of such antibody reagents, as well as procedures for preparing such labeled reagents.

Also provided are antibody reagents which can be used, and in many instances are critical, for constructing stable vancomycin calibrators and controls which can be used in assays to measure vancomycin concentration.

According to the present invention, the labeled reagents and the antibody reagents offer an advance in the art beyond previously known procedures when used in an immunoassay for the quantification of vancomycin in a test sample. Specifically, it was discovered that the antibody reagents of the present invention have essentially no cross-reactivity with the metabolites CDP-I and CDP-II. Moreover, the antibody reagents of the present invention can be used in the presence of polypeptides which stabilize the vancomycin molecule for the quantification of vancomycin. In the present invention, the presence of such polypeptides does not interfere with the quantification of vancomycin in a sample.

SUMMARY OF THE INVENTION

The present invention provides a method for the quantification of vancomycin in a test sample, wherein:
(a) the test sample is contacted with an antibody reagent having antibodies which are capable of specifically binding to vancomycin and are produced with an immunogen of FIG. 6 wherein P is an immunogenic carrier material, and X is a linking moiety of from 0 to 50 carbon and heteroatoms, including not more than ten heteroatoms, arranged as a straight or branched chain or cyclic moiety, saturated or unsaturated, with the provisos that not more than two heteroatoms may be directly linked in sequence, that the sequences cannot contain —O—O linkages, that cyclic moieties contain 6 or fewer members, and that branching may occur only on carbon atoms, and a labeled reagent of FIG. 8 wherein Q is a detectable moiety, and X is from 0 to 50 carbon and heteroatoms, including not more than ten heteroatoms, arranged as a straight or branched chain or cyclic moiety, saturated or unsaturated, with the provisos that not more than two heteroatoms may be directly linked in sequence, that the sequence cannot contain —O—O linkages, that cyclic moieties contain 6 or fewer members, and that branching may occur only on carbon atoms, to form a reaction solution; and
(b) measuring the amount of the labeled reagent in the reaction solution which either is or is not bound with an antibody as a function of the amount of vancomycin in the test sample.

The invention further provides the above method wherein fluorescence polarization is employed.

In a preferred method of the invention the antibody is produced with an immunogen of FIG. 6 and the labeled reagent is as shown in FIG. 8.

The invention further provides novel immunogens of FIG. 6 which are useful to produce antibodies which specifically bind vancomycin.

The invention further provides antibodies which are specific for vancomycin and have essentially no cross-reactivity with CDP I and CDP II and are capable of binding to any non-peptidic site on vancomycin. More specifically, the antibodies of the present invention do not compete with stabilizing peptides, specifically polypeptides used to stabilize vancomycin, for binding to the peptide binding site on vancomycin.

This invention also provides the hybridoma cell line designated as HB 11834 and monoclonal antibodies produced thereby. Such monoclonal antibodies are most preferred for the quantification of vancomycin, most preferably by fluorescence polarization.

The invention also provides stable calibrators for use in quantifying vancomycin. The calibrators of the present invention are in an aqueous solution and contain a polypeptide stabilized vancomycin molecule. The polypeptide does not interfere with the binding of an antibody to the vancomycin molecule.

Also provided are kits useful for the quantification of vancomycin in a test sample having antibody reagents and labeled reagents. Preferred kits have antibodies produced from an immunogen of FIG. 6; most preferred are monoclonal IgG antibodies produced from an immunogen of FIG. 5.

The present invention also provides synthetic procedures for preparing immunogens which are employed for the production of such antibody reagents, and for preparing such labeled reagents.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 16 shows the structures of vancomycin analogs and tracers.

DETAILED DESCRIPTION OF THE INVENTION

Figure 1:
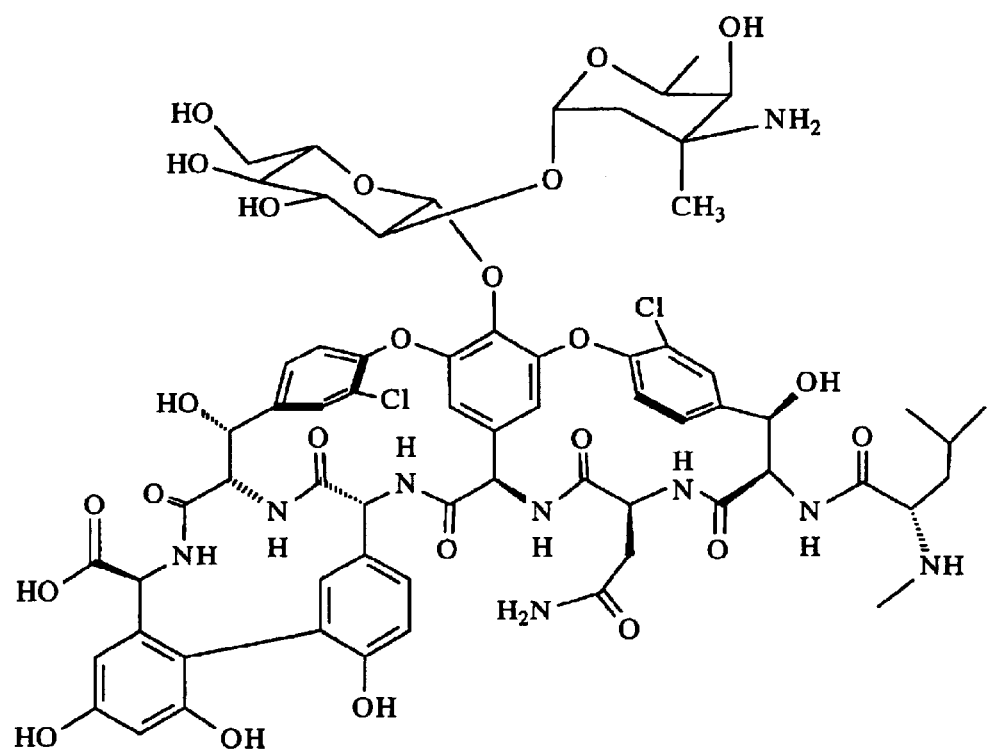
FIG. 1 shows the structure of vancomycin.
Figure 2:
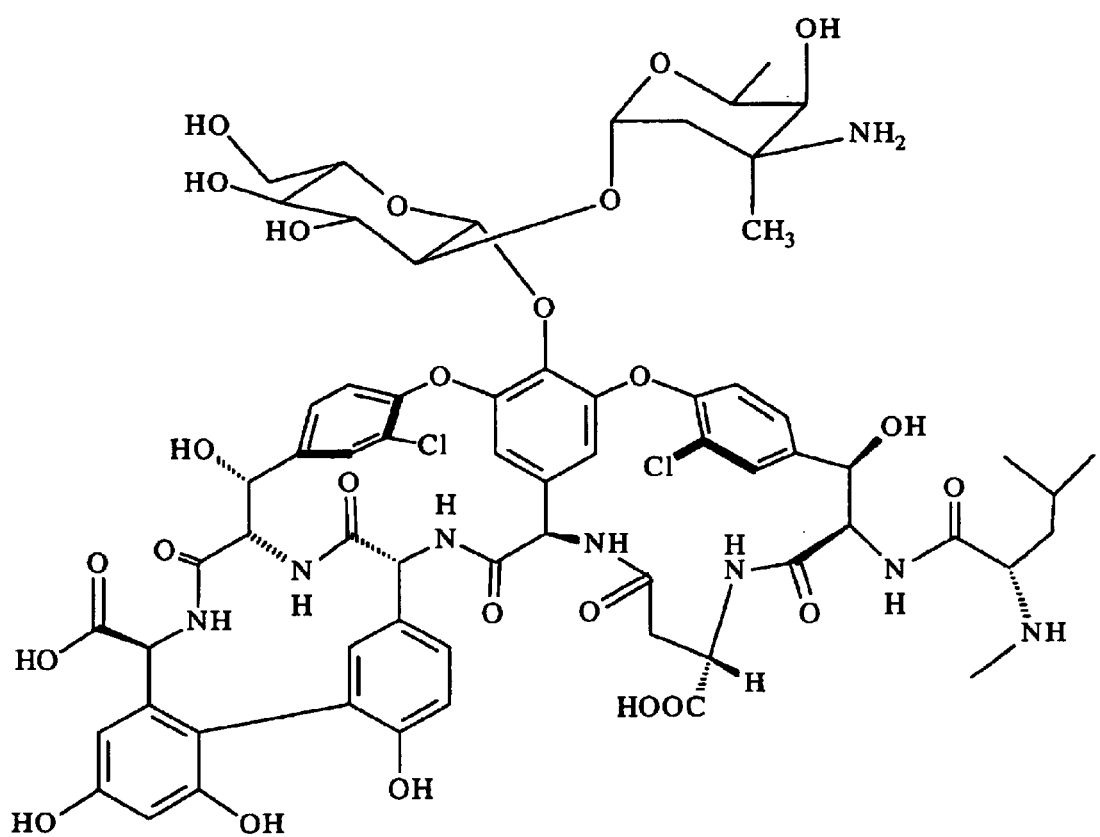
FIG. 2 shows the structure of one of the major metabolites of vancomycin, CDP-I.
Figure 3:
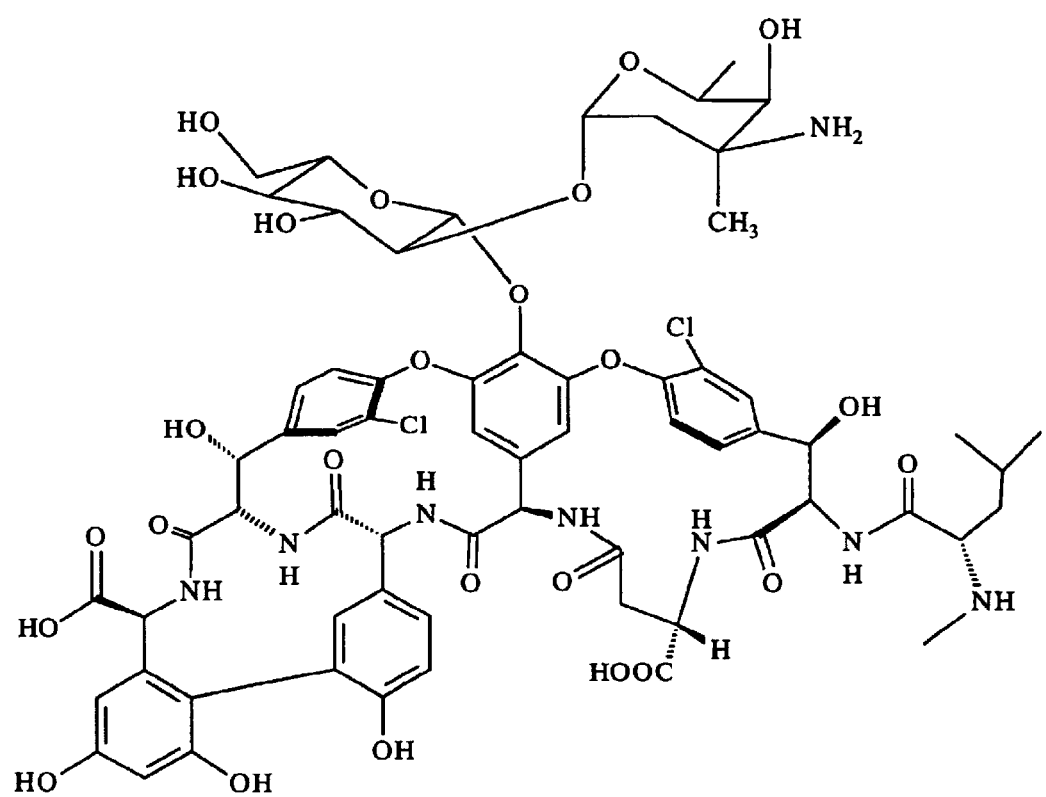
FIG. 3 shows the structure of another of the major metabolites of vancomycin, CDP-II.

As used in this specification and the attached claims, the following words shall have these respective meanings:

"Heteroatom" means nitrogen, oxygen, sulfur and phosphorous.

"$CHCl_3$" means chloroform, "$CDCl_3$" means deutero chloroform, "MeOH" means methanol, "DMF" means dimethylformamide, "$CH_2Cl_2$" means methylene chloride, "$Et_2O$" means diethyl ether and "DMSO" means dimethylsulfoxide.

"Linking moiety", "tether", "spacer", "spacer arm", and "linker are used interchangeably and are meant to define any covalently bound chemical entity that separates one defined substance (such as a hapten) from a second defined substance (such as an immunogenic carrier or detectable moiety).

"Stable" refers to the transformation of vancomycin to its degradation products, CDP-I and CDP-II in an aqueous environment as a function of time. As described herein, calibrators of the present invention are stable for no less than two (2) months.

"Essentially no cross-reactivity with CDP-I and CDP-II" means that the cross-reactivity of the antibodies of the present invention with the metabolites, CDP-I and CDP-II is below the sensitivity of an assay for vancomycin, as illustrated herein in Table 3.

"Non-peptidic site" refers to any site on the vancomycin molecule other than the peptide binding site.

The present invention provides immunogens, antibodies prepared from such immunogens, and labeled reagents which are suitable for use for the quantification of vancomycin. The specific quantification of vancomycin is accomplished by first contacting a test sample with a labeled reagent (also referred to herein as a tracer) of the present invention and an antibody reagent of the present invention, either simultaneously or sequentially in either order, and then measuring the amount of the labeled reagent which either has or has not participated in a binding reaction with the antibody reagent as a function of the amount of vancomycin in the test sample. The antibodies and labeled reagents of the present invention are especially useful in fluorescence polarization immunoassays (FPIA) for the specific quantification of vancomycin.

According to a preferred embodiment of the present invention, the labeled reagent and the antibody reagents are used in a fluorescence polarization immunoassay which combines specificity with the speed and convenience of homogeneous methods to provide a reliable quantification of vancomycin in a test sample and avoidance of interference from the major metabolites of vancomycin, CDP-I and CDP-II.

The test sample can be any naturally occurring bodily liquid, or an extract or dilution thereof, and includes, but is not intended to be limited to whole blood, serum, plasma, urine, feces, saliva, cerebrospinal fluid, brain tissue, and the like.

As is known to one of ordinary skill in the art, when preparing specific antibodies and complementary labeled haptens one needs to consider the chemical structure of both the immunogen used to elicit the antibody response and the labeled hapten. Traditionally, one attaches the hapten to the carrier protein through a site on the hapten that is remote from the unique features of the hapten that are critical for achieving selective antibodies. Likewise, when preparing a labeled hapten able to bind to such antibodies, it is customary to attach the label through the same site on the hapten as employed for linking the carrier protein to the hapten. One reason behind such an approach is that the carrier protein may sterically block access of the immune system to that part of the hapten. The complementary labeled hapten is synthesized by attaching its label to the same site on the hapten as the immunogen uses for attachment of its carrier protein, so as not to interfere with antibody binding to the critical features of the hapten.

Therefore, it was surprisingly and unexpectedly discovered that the vancomycin immunogens of the present invention, which are derived from different sites of attachment on vancomycin, lead to development of antibodies specific for vancomycin and an assay displaying an excellent cross-reactivity profile for the major metabolites of vancomycin. Among the most surprising discoveries is that, based on the limits of the sensitivity of the assay, the monoclonal antibody secreted by HB 11834 displays essentially no cross-reactivity with CDP, specifically, CDP-I and CDP-II. Additionally, it was also surprising to discover that this monoclonal antibody does not bind to the peptide binding site. This results in an improved assay for the quantification of vancomycin and allows for the use of stable calibrators and controls.

Synthesis of Immunogens

Figure 6:
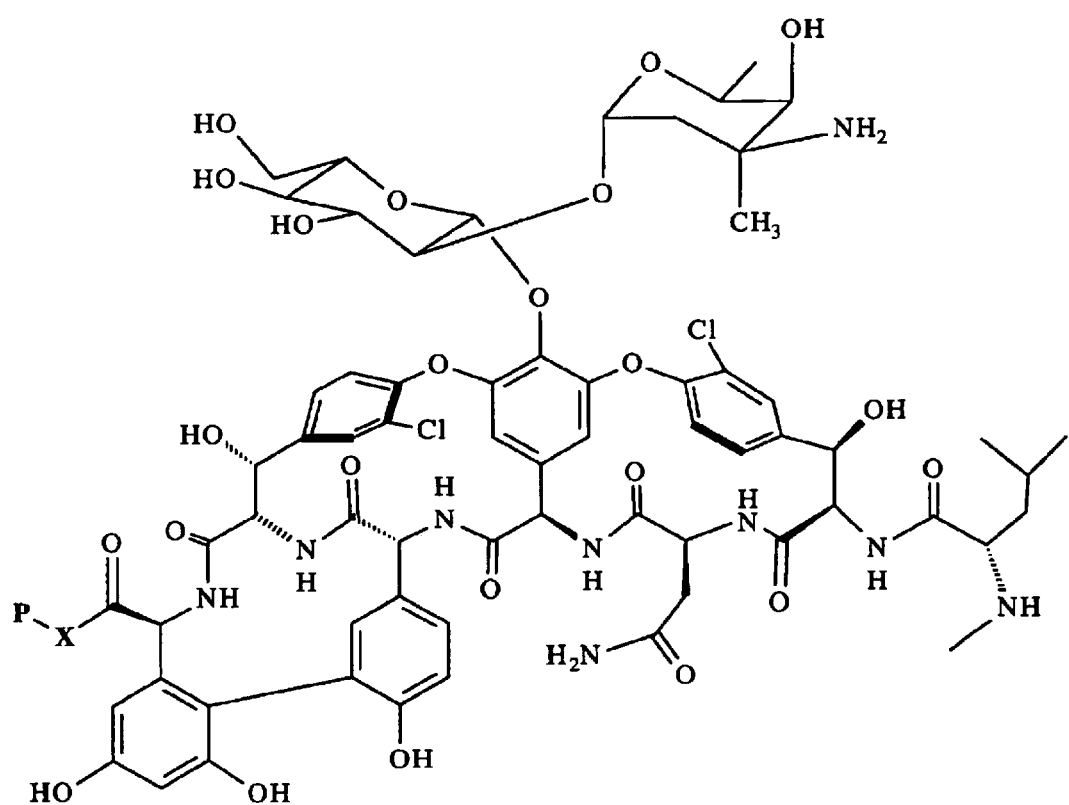
FIG. 6 shows the structure of the immunogen of the invention.

Antibodies of the present invention, both polyclonal and monoclonal, are produced with immunogens prepared from a vancomycin molecule which is conjugated to the carrier protein via the carboxylic acid terminal of vancomycin as shown in the general formula of FIG. 6 wherein P is an immunogenic carrier material and X is a linking moiety.

In the immunogens of the present invention, X is preferably a linking moiety consisting of from 0 to 50 carbon and heteroatoms, including not more than ten heteroatoms, arranged in a straight or branched chain or cyclic moiety, saturated or unsaturated, with the provisos that not more than two heteroatoms may be directly linked, that cyclic moieties contain six or fewer members, and that branching occur only on carbon atoms.

As would be understood by one skilled in the art, the immunogenic carrier material P, can be selected from any of those conventionally known. In most instances, P will be a protein or polypeptide, although other materials such as carbohydrates, polysaccharides, lipopolysaccharides, poly (amino)acids, nucleic acids, and the like, of sufficient size and immunogenicity can also be employed. Preferably, the immunogenic carrier material is a protein such as bovine serum albumin (BSA), keyhole limpet hemocyanin (KLH), thyroglobulin, and the like.

Figure 7:
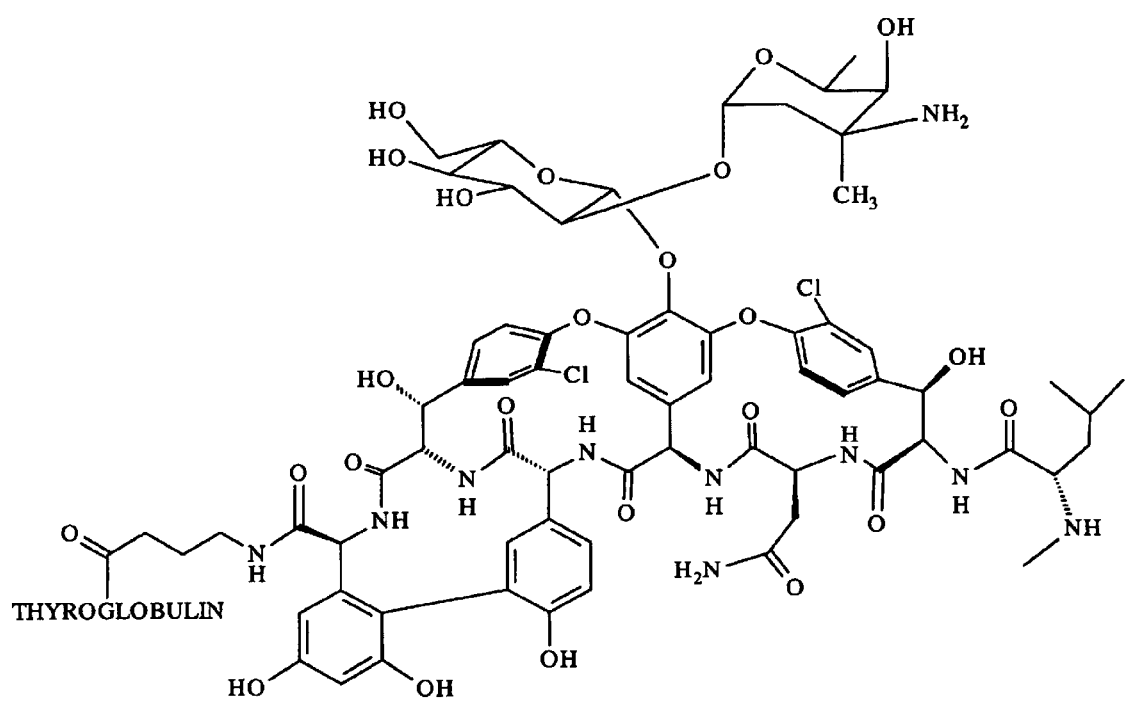
FIG. 7 shows the structure of the most preferred immunogen of the invention.

In the preferred immunogen, P is thyroglobulin and X is —NH($CH_2$)$_3$C (=O)—. The most preferred immunogen is shown in FIG. 7. However, the compound of FIG. 7 is not limited to a single conjugate of vancomycin and the immunogenic carrier, as one skilled in the art would realize. Rather, the ratio of vancomycin derivative to immunogenic carrier is defined by the number of chemically available functional groups on the immunogenic carrier P and controlled by the ratio of the two materials in the synthesis. The degree of substitution on P by the vancomycin derivative can vary between 1 to 100% of the available functional groups on the immunogenic carrier. The level of substitution is preferably between 10% to 95%; and more preferably, between 15% to 85%.

Figure 4A:
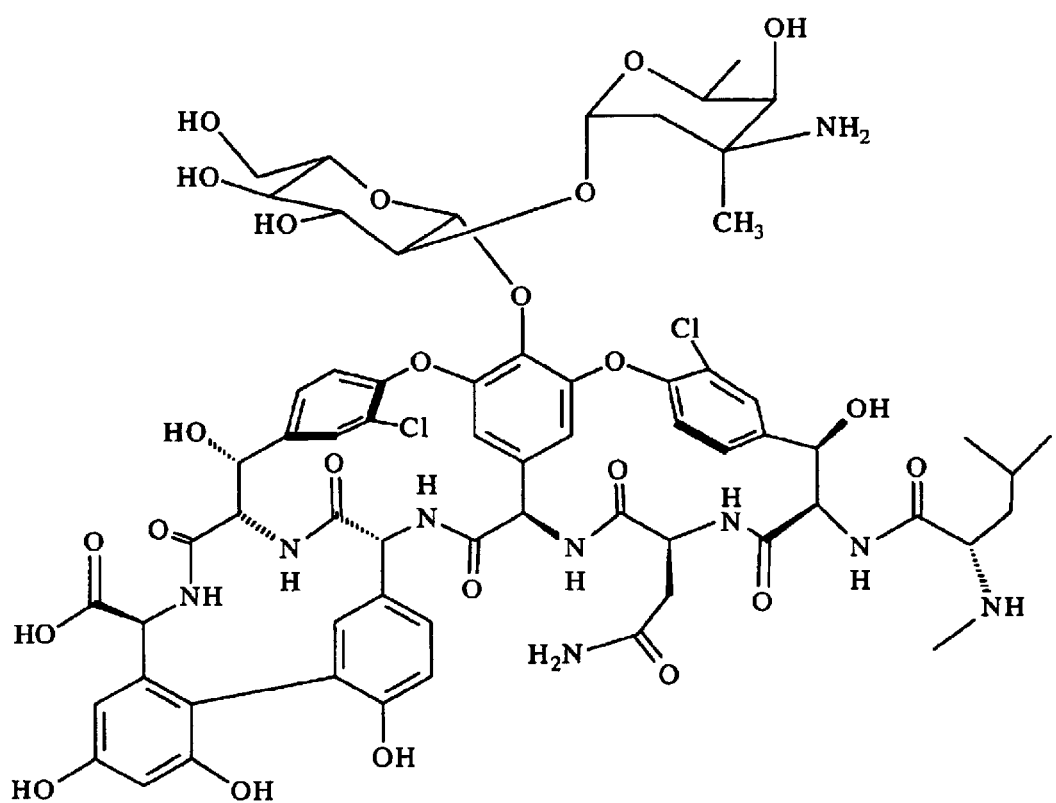
FIGS. 4a through 4c illustrate a representative synthetic pathway for coupling vancomycin to carrier protein.
Figure 4A:
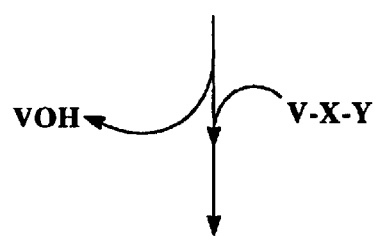
Figure 4B:
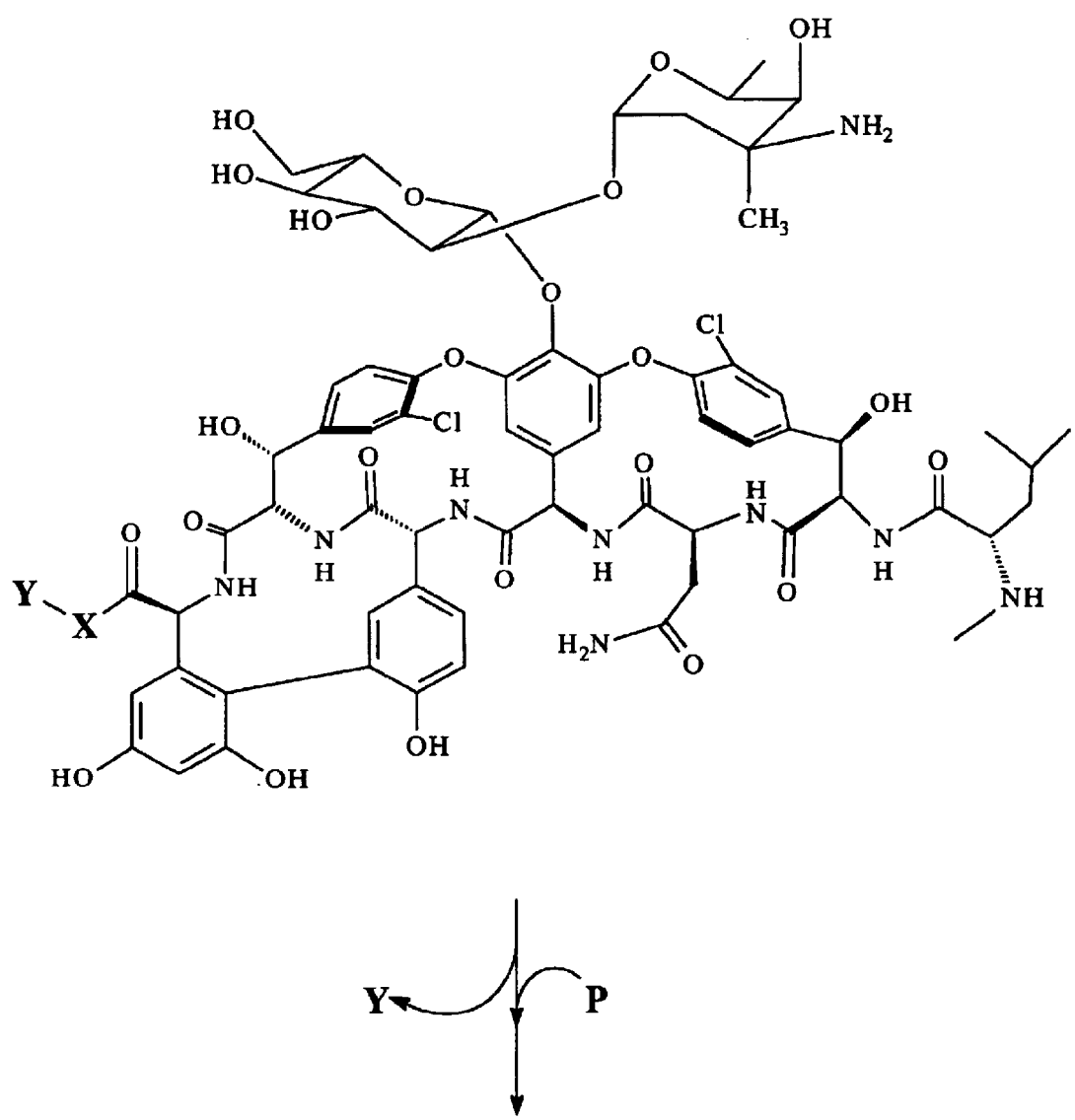
Figure 4C:
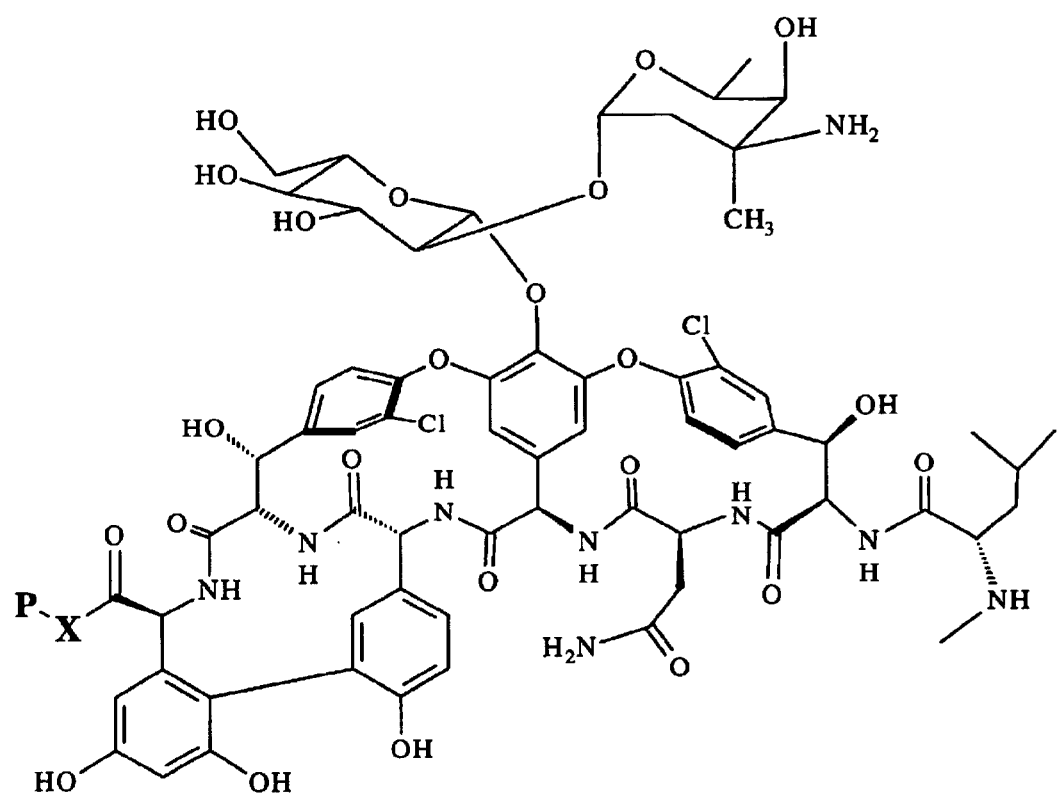
Figure 5A:
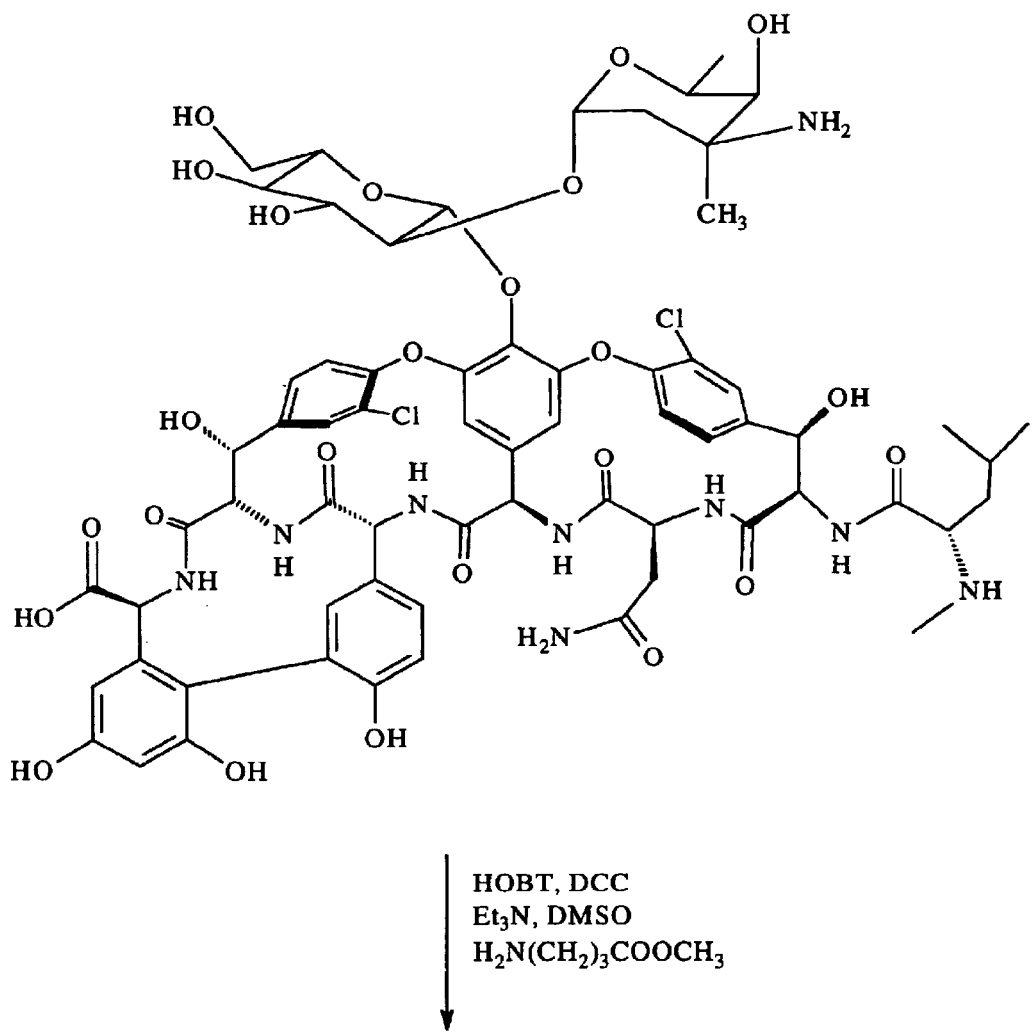
FIGS. 5a through 5d illustrate the synthetic pathway for coupling vancomycin to thyroglobulin according to the method of the present invention.
Figure 5B:
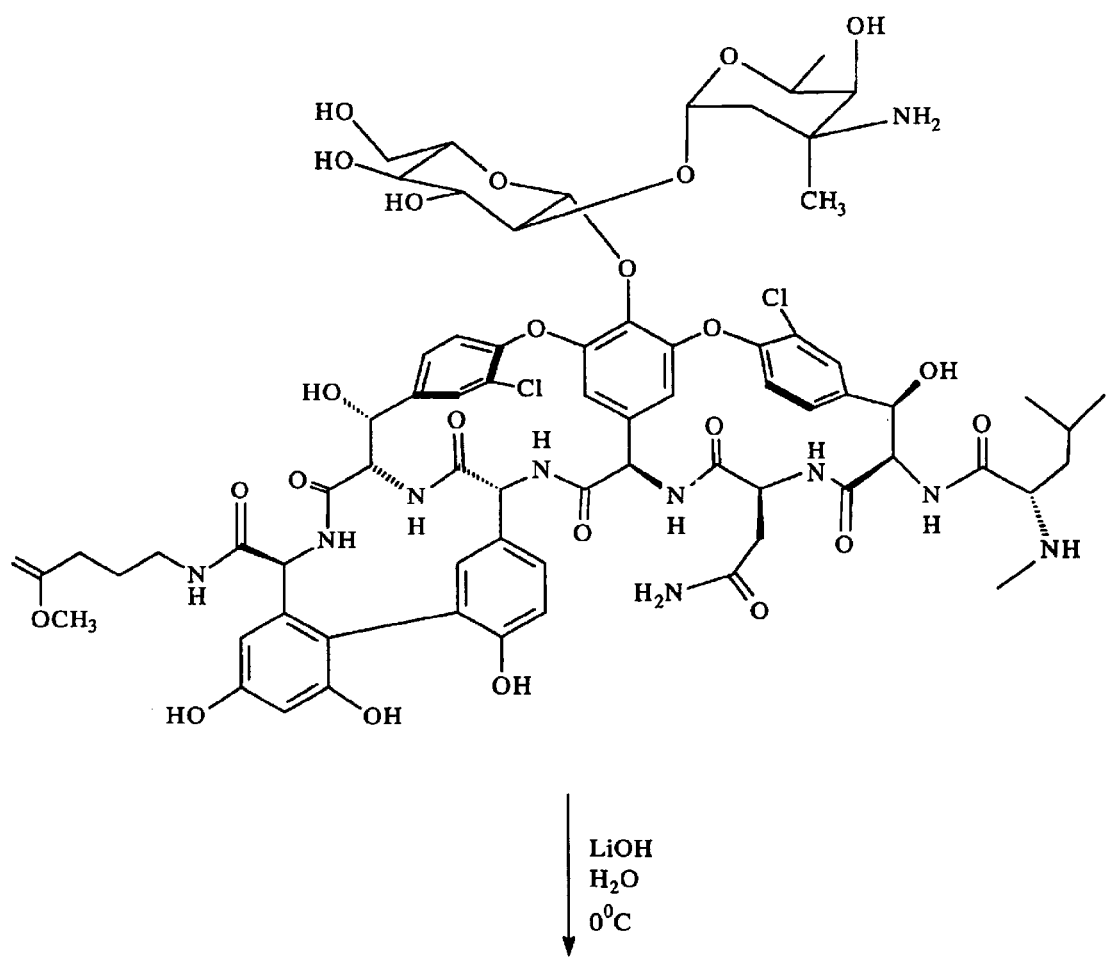
Figure 5C:
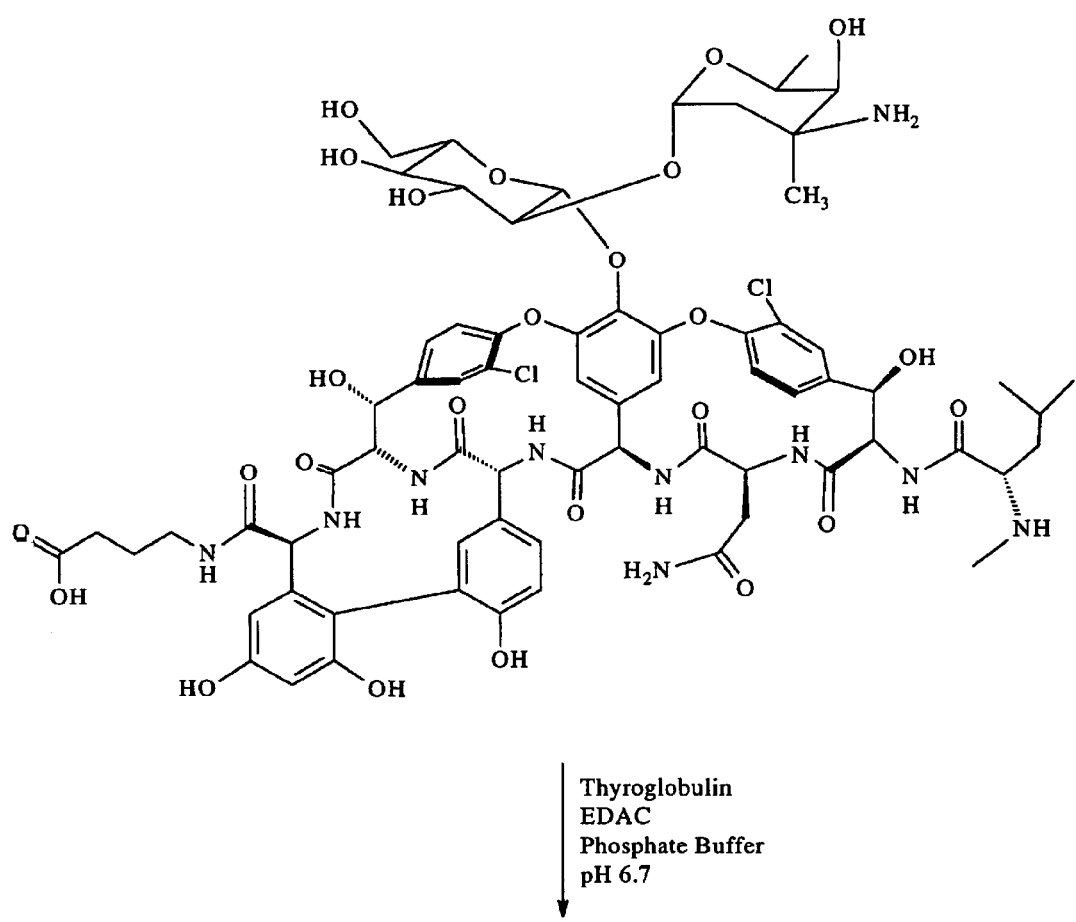
Figure 5D:
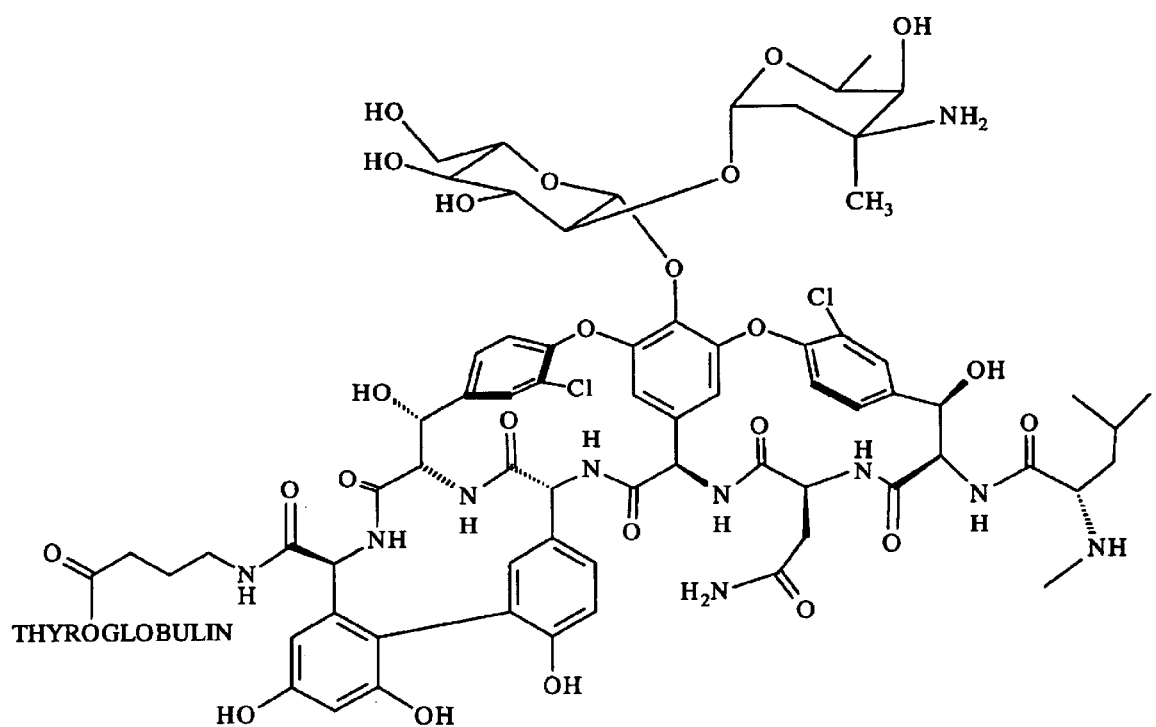

As stated above, the immunogenic conjugate of the present invention is prepared by coupling vancomycin to a carrier material via the carboxylic acid terminal of vancomycin. As shown in FIGS. 4a through 4c, vancomycin is coupled according to methods known to those skilled in the art with a bifunctional compound designated V-X-Y wherein X is a linking moiety and V- and —Y are functional groups one of which can react with the carboxylate of vancomycin (I) and the other with chemically available functional groups on P. Many bifunctional linkers are known in the art. For example, heterobifunctional linkers are described in, e.g., U.S. Pat. No. 5,003,883 to Bieniarz, et al. Heterobifunctional linkers may be preferred in some cases due to the specificity of their ends for one functional group or another. Likewise, for convenience in the synthesis of the immunogen, the functional groups V- and —Y may be protected, and deprotected at the desired time, following techniques well known to, or easily acquired by, those skilled in the art (see, e.g., T. W. Greene and P. G. M. Wutts, "Protective Groups in Organic Synthesis, $2^{nd}$ Ed." 1991, John Wiley and Sons).

Generally, in the preparation of the immunogens of the present invention, V is selected from the group consisting of —OH, -halo (—Cl, —Br, —I), —SH, or —NHR'—, where R' is selected from H, alkyl, aryl, substituted alkyl or substituted aryl. Y may be selected from the group consisting of carboxy (—C(=O)OH), amino (—$NH_2$), aldehyde (—CH(=O)), or azido (—$N_3$). As stated above, X is a linking moiety from 0 to 50 carbon and heteroatoms, including not more than ten heteroatoms, arranged in a straight or branched chain or cyclic moiety, saturated or unsaturated, with the provisos that not more than two heteroatoms may be directly linked, that the sequence V-X-Y cannot contain —O—O— linkages, the cyclic moieties contain six or fewer members, and that branching occur only on carbon atoms.

Referring now to the representative synthetic scheme shown in FIGS. 4a through 4c, the reaction of vancomycin (see FIG. 4a) with V-X-Y produces a tethered intermediate compound (FIG. 4b) having linking moiety X with a functional group Y. The functional group —Y, can be reacted in any of several ways known to those skilled in the art, with the functional groups on an immunogenic carrier. It is preferable to form amide bonds, which typically are quite stable. Amide bonds are formed by first activating the carboxylic acid moiety [Y=(—C(=O)OH)] of the spacer arm by reaction with an activating reagent such as 1,3-dicyclohexylcarbodiimide and an additive such as N-hydroxysuccinimide. The activated form (see FIG. 4b) is then reacted with a buffered solution containing the immunogenic carrier materials. Alternatively, the carboxylic acid group may be converted, with or without isolation, into a highly reactive mixed anhydride, acyl halide, acyl imidazolide, or mixed carbonate and then combined with the immunogenic carrier materials. As is readily apparent to one with ordinary skill in the art, there are many reagents that can be used to form amide bonds other than those listed above and such reagents require no special mention.

Alternatively, a spacer arm with a terminal amine functionality (Y=—$NH_2$) can be transformed into a highly reactive N-hydroxysuccinimide urethane by reaction with N,N'-disucinimidyl carbonate in a suitable solvent, such as acetonitrile or dimethylformamide. The resultant urethane is then reacted with the immunogenic carrier materials in a buffered, aqueous solution to provide an immunogen.

Additionally, a spacer arm with a terminal aldehyde functionality [Y=—CH(=O)] can be coupled to the immunogenic carrier materials in a buffered, aqueous solution and in the presence of sodium cyanoborohydride, by reductive amination according to methods known to those skilled in the art.

Alternatively, spacer arms containing an alcohol group [Y=—OH] can be coupled to the immunogenic carrier materials by first reacting it with phosgene or phosgene equivalent, such as di- or triphosgene or carbonyldiimidazole, resulting in the formation of a highly reactive chloroformate or imidazoloformate derivative (usually without isolation). The resultant active formate ester is then reacted with the immunogenic carrier materials in a buffered, aqueous solution.

Alternatively, when Y=—$N_3$, the tethered intermediate can be coupled to the immunogenic carrier by photolysis in aqueous buffered solution.

The preferred immunogen of FIG. 6 is thus prepared according to the scheme of FIGS. 5a through 5d. The carboxyl group of vancomycin (see FIG. 5a) is activated with dicyclohexylcarbodiimide and N-hydroxybenzotriazole (HOBT). Further reaction with the linker, 4-aminobutyric acid methyl ester [V=—$NH_2$, X=—($CH_2$)$_3$—, Y=—$CO_2$H] which after hydrolysis gives the tethered intermediate [X=—($CH_2$)$_3$—, Y=—$CO_2$H]. Y is then activated with 1-(3-dimethylaminopropyl)-3-ethylcarbodiimide (EDAC) and coupled to P. Those skilled in the art will recognize that other methods for peptide bond formation could be employed with equal success.

Thus, in the manner just described, vancomycin can, via this and other reactive sites on the molecule such as amines or alcohols, be coupled to immunogenic carrier materials by various conventional techniques known in the art where P is an immunogenic carrier material as described previously.

Furthermore, in a manner analogous to linking haptens to carrier materials, spacer arms can be conjugated to solid supports having functional groups such as amino, hydroxyl or carboxyl groups that are reactive in a complementary sense with reactive groups on the spacer arm. The result is a solid phase which can be used to separate or purify antibodies against the hapten. Such coupling techniques are also well known in the art.

The Antibodies of the Present Invention a. Production of Antibodies

The immunogens of the present invention may be used to prepare antibodies, both polyclonal and monoclonal, according to methods well known in the art. Generally, a host animal, such as a rabbit, goat, mouse, guinea pig, or horse is injected at one or more of a variety of sites with the immunogen, normally in a mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at $-20°$ C. Besides intact immunoglobulins, the term antibodies as used herein, includes antigen binding fragments of the immunoglobulins which may be produced by known methods, e.g., Fab, $F(ab')_2$ and Fv.

It is to be noted that the replacement of the commercially available antibody with the preferred antibody of the present invention alone improves the performance of the vancomycin assay.

It shall also be noted that the preferred method of the invention utilizes antibodies which do not bind metabolites that are not intended to be detected, to the extent such binding interferes with the accuracy of the assay, specifically, the metabolites, CDP-I and CDP-II.

b. The Specificity and Binding Affinity of the Antibodies of the Present Invention The antibodies produced by the immunogen of the present invention are specific for vancomycin and exhibit essentially no cross-reactivity with the metabolites, CDP-I and CDP-II.

Figure 20:
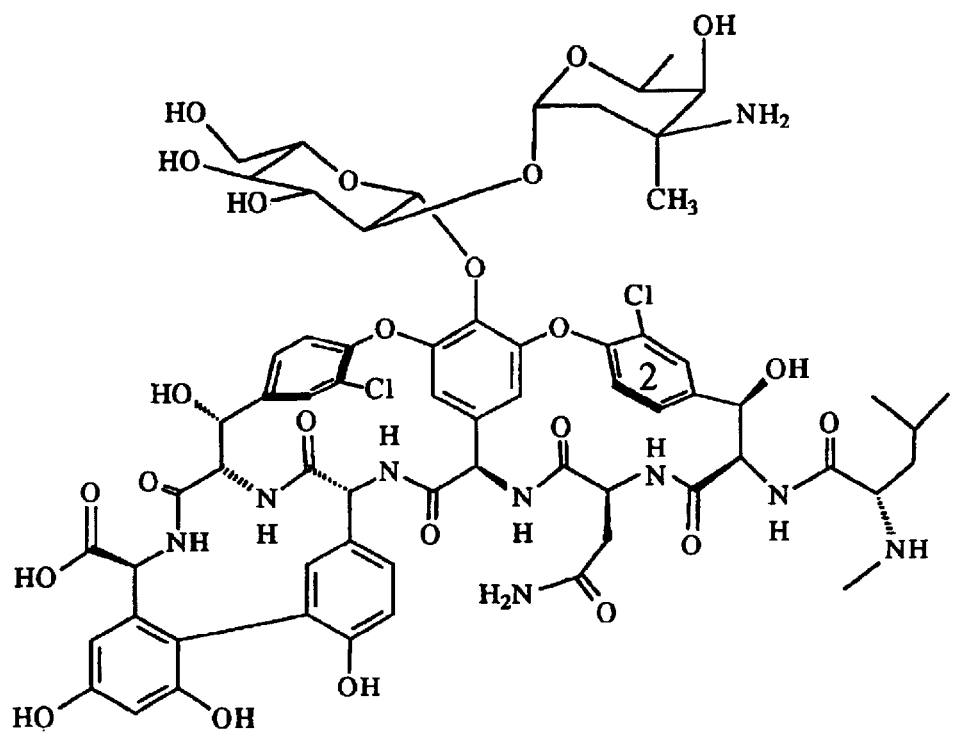
FIG. 20 shows the regions on vancomycin where the antibodies of the present invention bind. Specifically, the antibodies of the present invention bind to the regions shown in black, red and green. However, the antibodies of the present invention do not bind to the peptide binding region which is shown in blue.

In addition, the antibodies of the present invention bind to any non-peptidic site on the vancomycin molecule. The peptide binding site of vancomycin, where the antibodies of the present invention do not bind, is shown in blue in FIG. 20. The non-peptidic sites on the vancomycin molecule where the antibodies of the present invention do bind is shown in black, red and green in FIG. 20. Preferably, the antibodies of the present invention bind to the two sugar moieties (shown in red) in FIG. 20 and the chlorinated phenyl (shown in green) in FIG. 20.

Because the antibodies of the present invention do not bind to the vancomycin peptide binding site, the vancomycin peptide binding site is preserved for the binding of stabilizing peptides. The binding of peptides at the peptide binding site allows for the stabilization of vancomycin in aqueous solutions. Peptides that can be used to stabilize vancomycin are those polypeptides which are known to have a binding affinity for vancomycin. The preferred polypeptides are those containing at least 3 amino acid residues and contain the following fragment within its structure: α, ε-DiAc•L-lys•D-ala•D-ala.

The antibodies of the present invention, due to their binding affinity to sites other than the peptide binding site on the vancomycin molecule, can be used for constructing vancomycin calibrators and controls which can be used in assays to measure vancomycin concentration. The calibrators and controls of the present invention are in an aqueous solution and contain a polypeptide stabilized vancomycin molecule. One or more of the polypeptides described above can be used to stabilize the vancomycin molecule. The polypeptides used to stabilize the vancomycin molecule do not interfere with the binding of an antibody to the vancomycin molecule. The calibrators of the present invention are stable for at least two months, preferably six months, and most preferably for over one year.

Preparation of the Labeled Reagent

As noted above, the labeled vancomycin reagent of the present invention is prepared by attachment of the label at the secondary amino terminal of vancomycin, that is, a position which differs from the position at which the carrier protein is attached.

Figure 8:
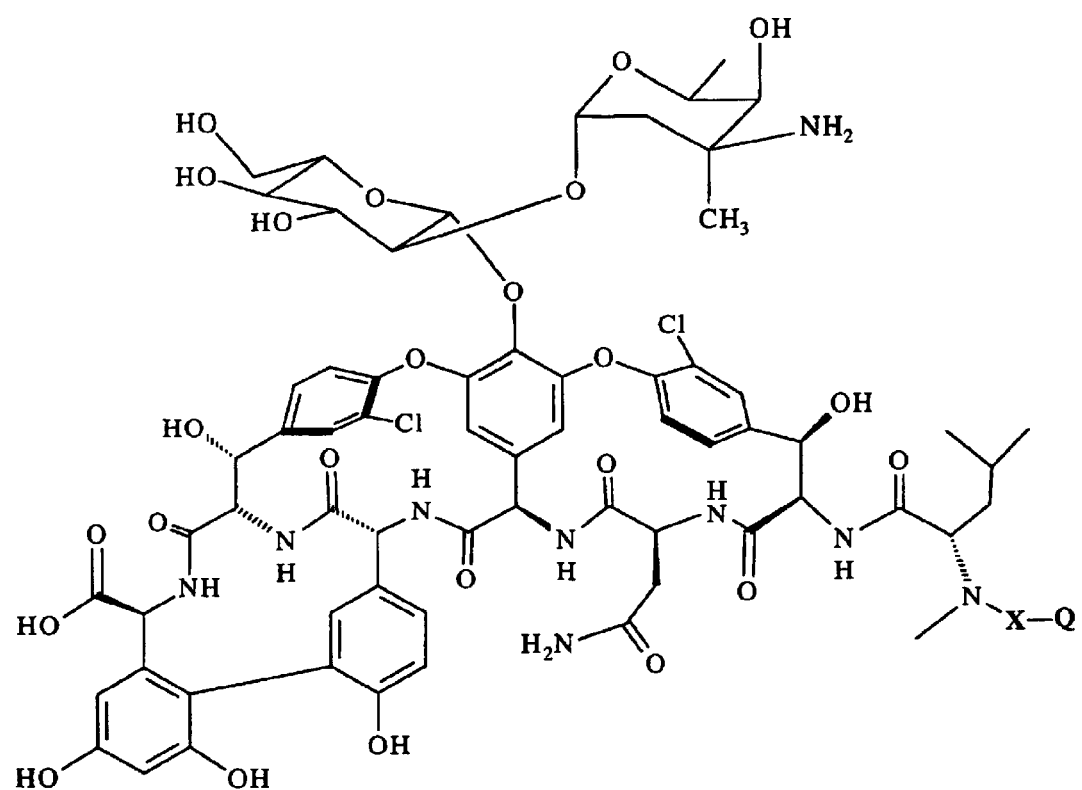
FIG. 8 shows the structure of the labeled reagent of the invention.

Labeled reagents of the present invention for vancomycin have the general formula shown in FIG. 8 wherein Q is a detectable moiety, such as a chemiluminescent or a fluorescent moiety; and X is a linking moiety. In the preferred labeled reagent, Q is a fluorescein derivative chosen from the group consisting of 4'-aminomethylfluorescein, 5-aminomethylfluorescein, 6-aminomethylfluorescein, 6-carboxyfluorescein, 5-carboxyfluorescein, 5 and 6-aminofluorescein, thioureafluorescein, and methoxytriazinylaminofluorescein, or a chemiluminescent moiety such as vancomycin-N-methylleucyl acridinium; and X is preferably a linking moiety consisting of from 0 to 50 carbon and heteroatoms, including not more than ten heteroatoms, arranged in a straight or branched chain or cyclic moiety, saturated or unsaturated, with the provisos that not more than two heteroatoms may be directly linked, that cyclic moieties contain 6 or fewer members, and that branching may occur only on carbon atoms. In the more preferred labeled reagent, Q is chlorotriazinylaminofluorescein and X=0, i.e., the vancomycin derivative is directly attached to the fluorescein derivative. The preferred labeled reagent of the invention has the structure shown in FIG. 9.

In a manner analogous to the synthesis of the immunogenic conjugate, the labeled reagents of the invention are synthesized from vancomycin by first differentially protecting the primary amino group (see, T. W. Greene and P. G. M. Wutts, "Protective Groups in Organic Synthesis, $2^{nd}$ Ed." 1991, John Wiley and Sons) followed by selectively reacting the secondary amino group with the detectable moiety.

Figure 10A:
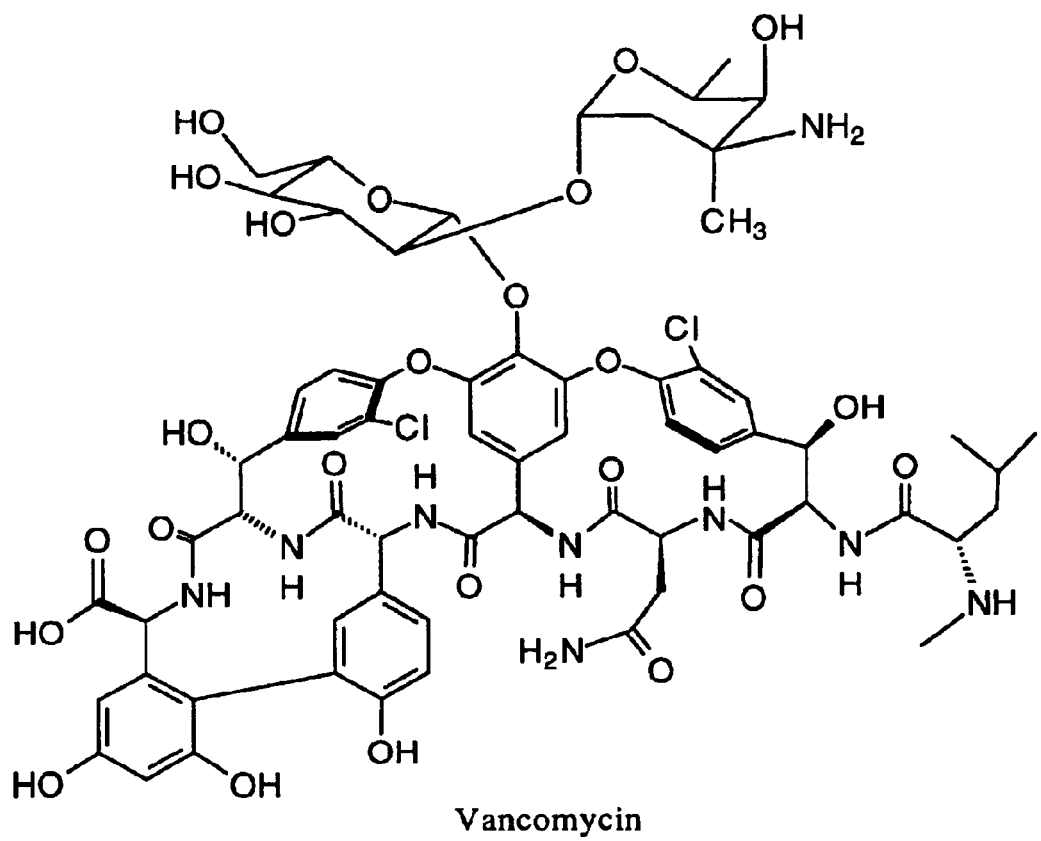
FIGS. 10a and 10b illustrate the synthetic pathway for coupling vancomycin to fluorescein according to the method of the present invention.
Figure 10A:
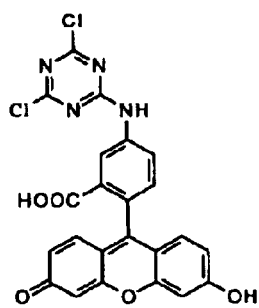
Figure 10B:
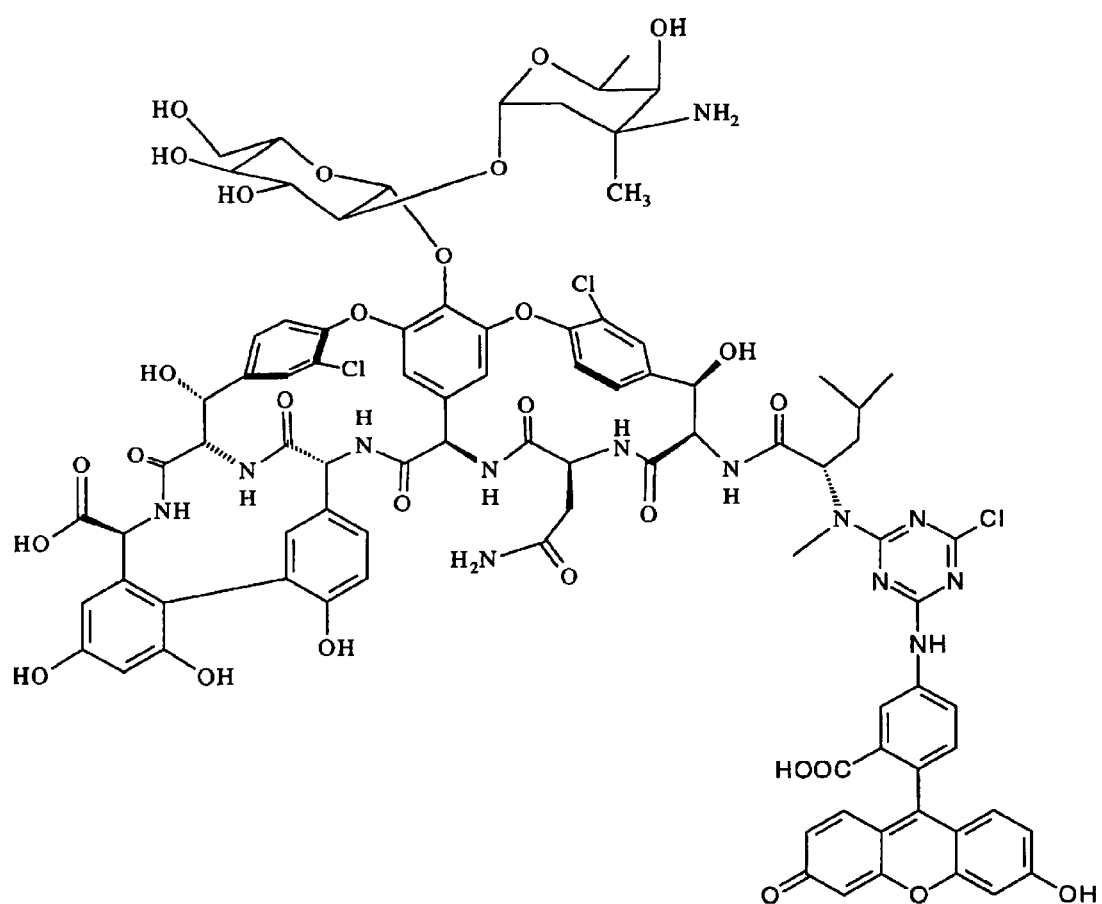

More specifically, the preferred labeled reagent can be synthesized as shown in FIGS. 10*a* and 10*b* by (i) reacting vancomycin base with dilute HCl at pH 6.0 to protect the primary amino group as a quaternized nitrogen followed by (ii) reacting it with dichlorotriazinylaminofluorescein (DTAF) to give the labeled reagent.

Figure 9:
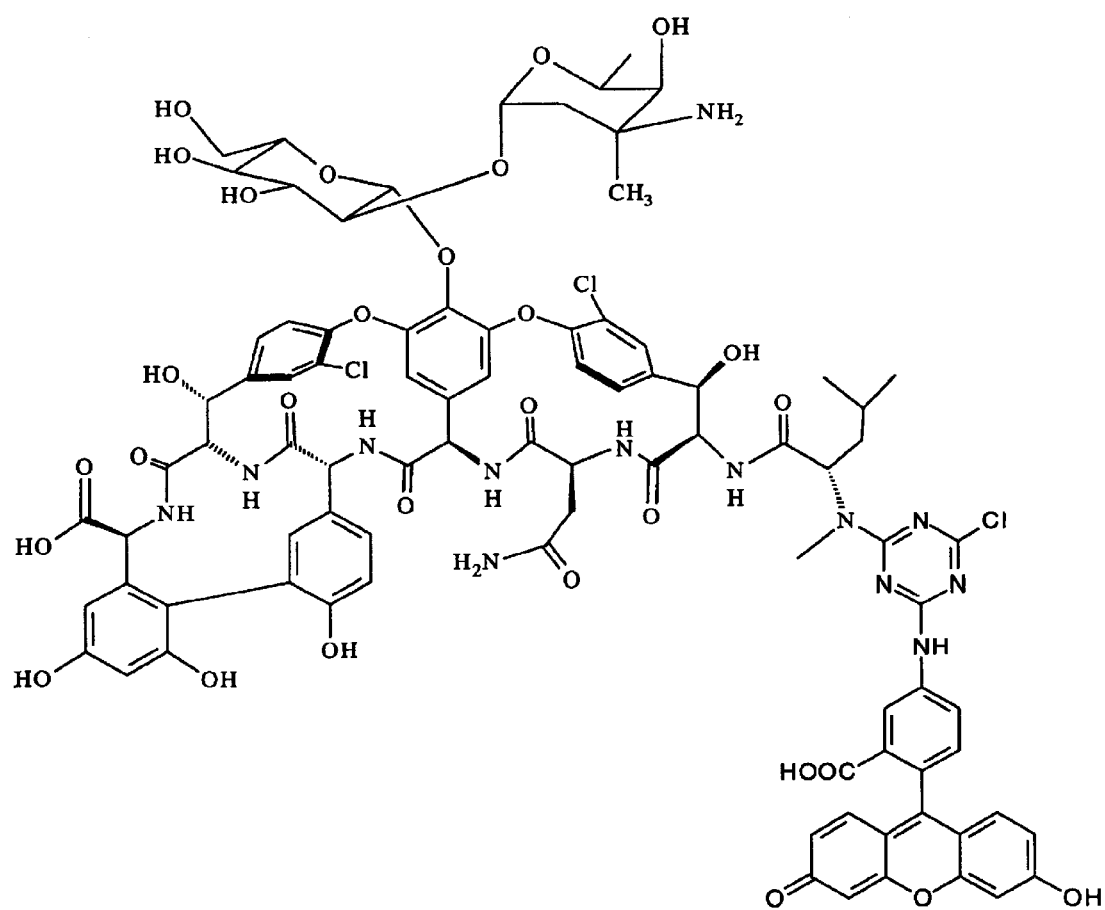
FIG. 9 shows the general structure of the most preferred labeled reagent of the invention.

In its most preferred aspect, the above synthetic methods are used to produce the labeled reagents of FIG. 9.

Vancomycin Assay Utilizing Fluorescence Polarization Immunoassay

By following a fluorescence polarization immunoassay (FPIA) format employing the reagents of the present invention, the concentration, or level, of vancomycin in a test sample can be accurately quantified. To perform a FPIA for the specific quantification of vancomycin, calibration curves are generated from calibrators having known concentration of vancomycin.

Generally, fluorescent polarization techniques are based on the principle that a fluorescent tracer, when excited by plane polarized light of a characteristic wavelength, will emit light at another characteristic wavelength (i.e. fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution. Therefore, within the time frame in which the ligand and tracer compete for binding to the antibody, the tracer and the ligand binding rates should yield an appropriate proportion of free and bound tracer with the preservation of important performance parameters such as selectivity, sensitivity, and precision.

When performing a fluorescent polarization immunoassay for the specific quantification of vancomycin according to the present invention, a test sample suspected of containing vancomycin is contacted with an antiserum or monoclonal antibodies prepared with immunogens according to the present invention, in the presence of labeled reagent of the present invention. Plane polarized light is then passed through the solution to obtain a fluorescent polarization response and the response is detected as a measure of amount of vancomycin present in the test sample The fluorescence polarization assays can be conducted in commercially available automated instruments (e.g., AxSYM®, TDX®, and TDXFLX®, Abbott Laboratories).

According to the present invention, it has been unexpectedly and surprisingly found that superior fluorescence polarization immunoassay results for the quantification of vancomycin are obtained when employing an antibody derived from the immunogen shown in FIG. 6 with the fluorescent labeled reagent shown in FIG. 8.

In particular, it was unexpectedly and surprisingly found that the use of the labeled reagent of FIG. 9 in combination with a monoclonal antibody produced in response to the immunogen of FIG. 7, resulted in an assay which shows very low, essentially zero, (that is, below the limits of the sensitivity of the assay) cross-reactivity to the major metabolites of vancomycin, CDP-I and CDP-II. Most preferred is the fluorescence polarization method which employs monoclonal IgG antibody produced by the hybridoma designated ATCC HB 11834.

The amount of tracer bound to the antibody varies inversely to the amount of vancomycin present in the test sample. Accordingly, the relative binding affinities of vancomycin and the tracer to the antibody binding site, are important parameters of the assay system.

Other Assay Formats

Figure 21:
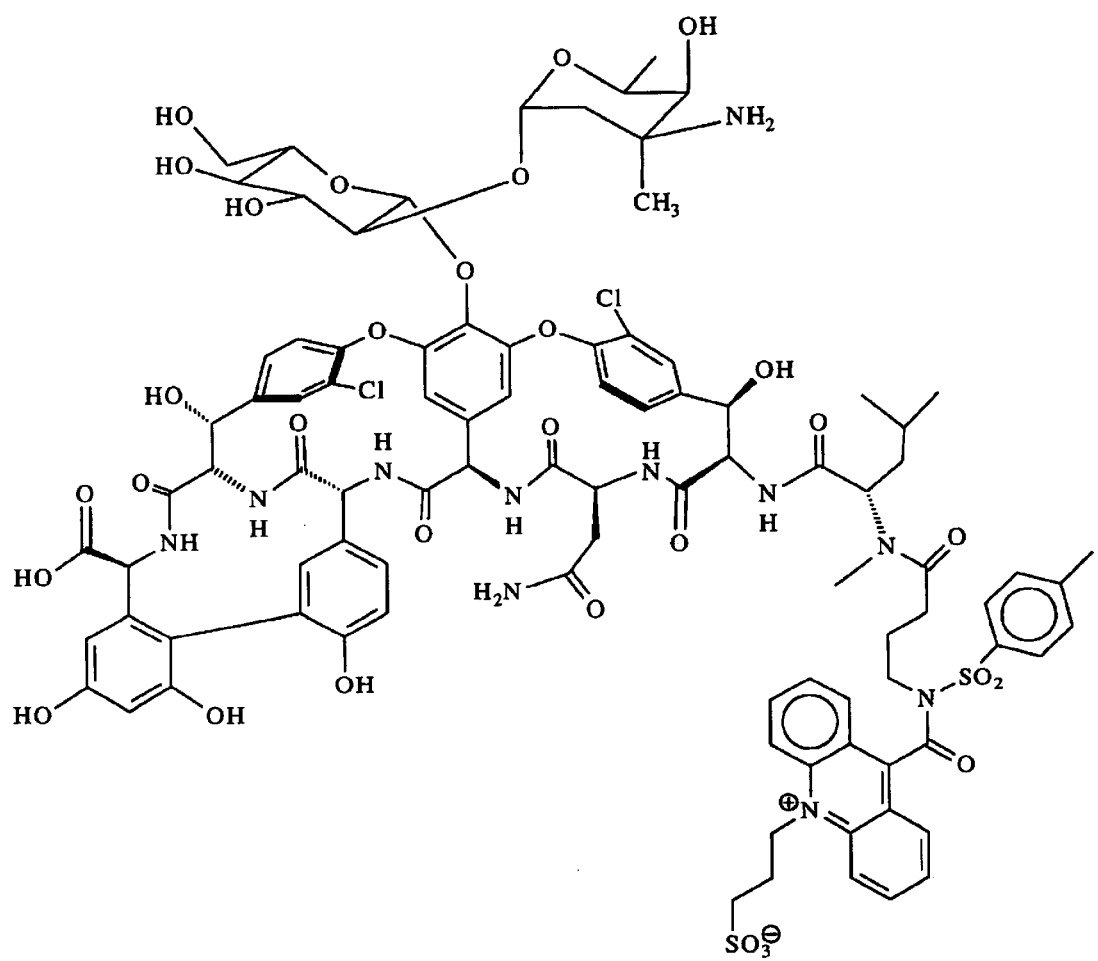
FIG. 21 shows the chemiluminescent tracers, vancomycinyl-N-methylleucyl acridinium.

In addition to fluorescence polarization immunoassays, various other immunoassay formats can be followed for the quantification of vancomycin according to the present invention. Generally, such immunoassay systems depend upon the ability of an immunoglobulin, i.e., a whole antibody or fragment thereof, to bind to a specific analyte from a test sample wherein a labeled or detectable reagent is employed to determine the extent of binding. Such detectable labels include, but are not intended to be limited to, enzymes, radiolabels, biotin, toxins, drugs, haptens, DNA, RNA, liposomes, chromophores, chemiluminescens such as, but not limited to those shown in FIG. 21, colored particles and colored microparticles, and fluorescent compounds such as those described earlier.

Typically, the extent of binding in such immunoassay system formats is determined by the amount of the detectable moiety present in the labeled reagent which either has or has not participated in a binding reaction with the analyte and requires that the amount of the detectable moiety detected and measured can be correlated to the amount of analyte present in the test sample. For example, in a competitive immunoassay system, the substance being measured (often referred to as a ligand) competes with a substance of close structural similarity to that of the ligand and which is coupled to a detectable moiety (often referred to as a tracer) for a limited number of binding sites on antibodies specific to the portion or portions of the ligand and tracer with structural similarity.

Test Kits

A test kit according to the present invention includes reagents necessary to perform a desired immunoassay for the quantification of vancomycin in a test sample. The test kit may be presented in a commercially packaged form as a combination of one or more containers holding the necessary reagents, and/or as a composition or admixture where the compatibility of the reagents will allow. Preferably, a test kit includes all reagents, standards, buffers, diluents, etc. which are necessary to perform the assay.

Particularly preferred is a test kit for the fluorescent polarization immunoassay quantification of vancomycin in a test sample, which includes fluorescent tracer compounds and antibodies as described above for the quantification of vancomycin. It is to be understood that the test kit can, of course, include other materials as are known in the art and which may be desirable from a user standpoint, such as sample pretreatment solutions, buffers, diluents, standards, and the like.

The present invention will now be illustrated, but is not intended to be limited to, the following examples.

EXAMPLE 1

Synthesis of Vancomycin Immunogen a) Synthesis of Methyl-4-amino Butyrate 4-amino butyric acid (5.00 g, 48.5 mmol) is taken in a 200 mL round bottom flask. Dimethoxy propane (80 mL, 65 mmol) is added to the flask with stirring. Concentrated hydrochloric acid (15 mL) is added to the reaction and stirred at room temperature overnight. Solvents are removed under reduced pressure on a rotary evaporator without heating. The solid is dissolved in a minimum amount of MeOH and is reprecipitated with ether. The precipitated solid is filtered under suction and washed with $Et_2O$ (2×50 mL). The solid (yield: 6.9 g (96%)) is then dried under vacuum.

$^1$H NMR of the free amine ($CDCl_3$): 2.1 (quintet, 2H), 2.5 (triplet, 2H), 3.2 (broad triplet, 2H), 3.7 (singlet, 3H), 8.1 (singlet, 2H).

b) Synthesis of Vancomycin-amino Butyrate Derivative

Vancomycin (500 mg, 0.34 mmol) base is taken in a 25 mL round bottom flask. DMSO (4 mL) is added and stirred, with warming as necessary, until a clear solution results. Methyl-4-amino butyrate HCL from Example 1(a) (506 mg, 3.4 mmol) is added to the reaction followed by hydroxybenzotriazole (105 mg, 0.69 mmol) and triethylamine (0.0976 mL, 0.69 mmol). Reaction is stirred at room temperature for 3 to 7 days under $N_2$. Reaction is followed by HPLC. After the starting material had been consumed, the precipitated solid is removed by filtration and the filtrate is purified by reverse phase HPLC using a C-18 column as described below. The collected fractions are lyophilized (yield:310 mg).

Analytical HPLC conditions are as follows: the column is 7.8 mm×300 mm C-18 (BONDAPAK C-18, sold by Waters, Marlborough, Mass.) with a continuous gradient mobile phase of acetonitrile: ammonium acetate (50 mM) (10% acetonitrile to 50% acetonitrile developed over 15 minutes) at a flow rate of 3.0 mL/minute. Detection is at 254 nm.

Preparative HPLC conditions are as follows: the column is 19 mm×250 mm C-18 (DYNAMAX 60A C-18, Rainin, Woburn, Mass.) with a continuous gradient mobile phase of acetonitrile: ammonium acetate (50 mM) (10% acetonitrile to 50% acetonitrile developed over 15 minutes) at a flow rate of 8.0 mL/minute. Detection is at 254 nm.

Mass Spectrometry (MS): Electron Spray Ionization (ESI) MH$^+$ 1547, (MH$_2$)$^{2+}$ 774.

c) Synthesis of Vancomycin Hapten

The vancomycin-amino butyrate derivative from Example 1(b) (165 mg, 0.1 mmol) is dissolved in DMF/Water (2 mL:3 mL) is a 25 mL round bottom flask. The flask is cooled to 0° C. and LiOH was added and stirred for 2 hours and warmed to room temperature and followed by HPLC. After the starting material has been consumed the reaction is directly purified by preparative HPLC using a reverse phase column. The solvent is lyophilized to give the product (yield: 160 mg). Both analytical and preparative HPLC are as stated above.

Mass Spectrometry (MS): ESI MS gives (MH)$^+$ at 1533 indicating the correct molecular weight of the hydrolyzed linker attached to vancomycin.

d) Synthesis of Immunogen

Thyroglobulin (100 mg, 0.0002 mmol) is dissolved in sodium phosphate monobasic buffer (5 mL, pH adjusted to 6.7 with dilute NaOH). Vancomycin hapten from Example 1(c) (50 mg, 0.0321 mmol) is added followed by EDAC (9.2 mg, 0.0482 mmol). The resultant reaction is stirred for 2 days at room temperature. The contents are transferred to a membrane and dialyzed with 0.1 M Na$_2$HPO$_4$ buffer (monobasic pH 7.8 adjusted with NaOH) for 2 days changing the solvent every 4 hours. The contents in the dialysis bag are lyophilized to yield 130 mg of the desired immunogen.

EXAMPLE 2

Production of Anti-vancomycin Antibody 15-109-592

A female, 6–8 weeks old, RBF/DnJ mouse (Jackson Laboratories, Bar Harbor, Me.) is immunized with the vancomycin immunogen of Example 1 emulsified with Freund's adjuvant (Difco, Detroit, MI). The primary immunization is administered with Freund's Complete Adjuvant and subsequent boosts with Freund's Incomplete Adjuvant. The animal boosting interval for this long term immunized animal is at weeks, 1, 3, 5, 12, 17 and 24 with the respective dosage level at 25, 12.5, 12.5, 10, 10 and 10 μg per animal at one subcutaneous site and one intraperitoneal site for the first three boosts and at two subcutaneous sites each for the last three boosts. Periodically, bleeds are made to confirm that an antibody response is developing. The animal was allowed a 7 week rest period before a 10 μg boost was administered to the spleen 3 days prior to fusion.

On the day of the fusion, the mouse is euthenized by a quick cervical dislocation and the spleen is removed. The splenocytes are washed one time in Iscove's Modified Dulbecco's Medium (IMDM) (Gibco, Grand Island, N.Y.) and centrifuged at 1000 RPM for 10 minutes. The pelleted splenocytes are combined with SP2/0 myeloma cells (Dr. Milstein, Cambridge, UK) at 1:1 ratio, washed in IMDM, and centrifuged. The supernatant is removed and 1 mL of 50% polyethylene glycol (PEG; American Type Tissue Culture Collection, Rockville, Md.) is added to the pellet for 1 minute as the pellet is resuspended in IMDM containing hypoxanthine, aminopterin, thymidine (HAT Gibco) and 15% Fetal Bovine Serum (FBS; Hyclone Labs, Logan, Utah). To enhance the fusion frequency, 0.5% *Salmonella typhimurium* mitogen v/v (STM; RIBI immunochem Research, Inc., Hamilton, Mont.) and 1% v/v ORIGEN (Igen, Rockville, Md.) are added to the fusion cell suspension and plated into 24 well tissue culture plates.

The primary screening of the fusion occurred on day 10 confluent cultures. A commercial assay (TDX®; Abbott Laboratories) is used to detect anti-vancomycin reactivity in supernate samples. The tissue culture supernate is loaded in duplicate into the sample well and 10 μl of either the A calibrator (0 μg/mL vancomycin) or the F calibrator (100 μg/mL vancomycin) from the commercial calibrator kit is loaded into the pre-dil well. Diluent buffer is placed in the S and P pots of the reagent pack and the commercial tracer is used in the T pot. Because hybridoma culture supernatant are very dilute, sample volume is increased to 90 μl. The polarization of the samples is measured and only one hybrid 15-109, is identified as specific to vancomycin as measured by a decrease in polarization in the presence of the F calibrator (See Table 1). This is due to the free vancomycin binding to the antibody and blocking the tracer from binding, therefore causing a decrease in signal.

TABLE 1

| Sample | mP @ 0 μg/ml[a] | mP @ 100 μg/ml |
|---|---|---|
| 15–109 | 100.74 | 54.42 |
| Negative Control[b] | 58.32 | 57.91 |
| Positive Control[c] | 328.38 | 80.30 |

[a]μg/ml Vancomycin
[b]Negative Control is an irrelevant antibody tissue culture supernate.
[c]Positive Control is Vanco clone 3-266-279 Tissue Culture Supernate.

Hybrid 15-109 is cloned by limiting dilutions from 1–100 to 1–100,000. The cloning media is IMDA with 10% v/v FBS and 1% v/v HT Supplement (Gibco). A 200 μl cell suspension is added to each well of a 96-well tissue culture plate.

The hybrid, now designated 15-109-133, is selected for further evaluation based on additional screening of the clone supernate of confluent cultures.

The monoclonal antibody hybrid 15-109-133 is first concentrated 10-fold using an Amicon filtration system. Then, the raw antibody (the antibody is still in fetal bovine serum) is cut using saturated ammonium sulfate (50%). The solution is then centrifuged at 4000 RPM (revolution per minute) and the supernate is discarded. The pellet is resuspended into PBS (pH 7.4) at a volume ¹⁄₁₀th the original volume after concentration. The antibody solution is then dialyzed in PBS (pH 7.4) and after dialysis is diluted using the commercial buffer (phosphate, azide, and bovine gamma globulin buffer) as follows: straight, 1:2, 1:4, 1:8, 1:16, and 1:32. The samples are run in duplicates in the sample well using a sample volume of 10 (100 μL) instead of 2 (20 μL) using the same Mode 1 vancomycin assay previously discussed. The instrument calculates the mP (millipolarization values) as described previously and the dilution of antibody generating the highest mP is chosen as the dilution of antibody to use in the S pot (antibody pot) in the reagent kit. The antibody is diluted into phosphate buffer including 10% glycerol and 5% BSA. The tracer pot contains the existing market tracer re-purified by HPLC and diluted in a Tris buffer (Plus 0.7% SDS and 0.5% LDS). This purified tracer is diluted to 1.7 μg/mL in the tracer pot. The popper consists of 20 mM copper sulfate and 2.5% 5-SSA. This reagent pack is loaded into the instrument with vancomycin (analyte) at 0, 5, 10, 25, 50 and 100 μg/mL as the calibrators run in duplicates along with controls at 7, 35, and 75 μg/mL. Assay 16 with Mode 1 pipetting is used on the instrument and a standard curve is calibrated and stored. CDP-I samples at various concentrations are run to ensure no CDP-I cross reactivity exists.

Based on the further screenings, a clone, now designated 15-109-592, is selected for deposit.

The isotype of the monoclonal antibody secreted from the cell line identified as 15-109-592 was determined on a antibody isotyping kit (Mouse Monoclonal, Southern Biotech, #5080-05, Birmingham, Ala.). The assay is performed according to the vendor recommendations and the results indicate an isotype of IgGl, kappa light chain.

Cell Line Deposit

In accordance with the Budapest Treaty, the hybridoma cell line, designated as hybrid 15-109-592, is deposited with the American Type Culture Collection (ATCC), 10801 University Boulevard, Manassas, Va. 20110-2209, United States of America. The deposit date is 16 February 1995 and the ATCC number assigned to the cell line is HB 11834. The deposit will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §1.801–1.809, including providing an indication of the viability of the sample.

EXAMPLE 3

Synthesis of Vancomycinchlorotriazinylaminofluorescein Tracer

Vancomycin base (576 mg, 0.4 mmol, 1.5 eq) is dissolved in DMF (8 mL) (with warming if necessary to 40° C.) in a 50 mL round bottom flask with a wide mouth. A small pH electrode is inserted to monitor the pH of the reaction. A solution of dichlorotriazinylaminofluorescein HCL (DTAF; 132 mg., 0.26 mmol, 1 eq.) in DMF (2 mL) is added to the flask. The reaction turns orange-yellow and the pH dropped to 6.0±0.5 and is stirred overnight while maintaining this pH. Reaction products are monitored by analytical HPLC. After all the DTAF had been consumed DMF is removed under vacuum to about 2–3 mL. The remainder is purified by HPLC. Appropriate fractions are collected and the solvent is lyophilized to give an orange yellow powder (yield: 350 mg).

Analytical HPLC conditions are as follows. The column is 3.9 mm×300 mm C-18 (DYNAMAX C-18, Rainin) with a continuous gradient mobile phase (A=ammonium acetate; B=acetonitrile (50 mM); % B=10, % B=50 developed over 15 minutes) at a flow rate of 1.5 ml/minute. Detection is at either 254 or 486 nm.

Preparative HPLC utilizes the same conditions as above with a 19 mm×250 mm C-18 column (DYNAMAX C-18, Rainin).

MS: ESMS gives $MH^+$ at 1908, $(MH_2)^{2+}$ at 953.

EXAMPLE 4

Fluorescence Polarization Immunoassay For Vancomycin

The tracer (Example 3) and monoclonal antibody #15-109-592 (Example 2) are optimized to perform similar to or better than TDX®/TDXFLX® Abbott Vancomycin assay with the advantage of no CDP-I cross reactivity in the presence of vancomycin. As discussed previously, by adding a constant concentration of antibody and tracer to the test sample, the ratio of vancomycin-antibody complexes to tracer-antibody complexes that are formed is directly proportional to the amount of vancomycin in the sample. When the mixture is excited with linearly polarized light and the polarization of fluorescence emitted by unbound tracer and tracer-antibody complexes is measured, one is able to quantitate or qualitate the presence of vancomycin in a test sample. The results can be quantified by net millipolarization units (mP) and span. Net millipolarization indicates the polarization detected when a maximum amount of tracer is bound to the antibody (i.e., in the absence of vancomycin). The higher the net mP units, the better the binding of the tracer to the antibody. Assay span is the difference between the net millipolarization values obtained when the maximum tracer is bound in the absence of any vancomycin and the net millipolarization obtained when a specific amount of vancomycin is present in a test sample. The millipolarization units are automatically interpolated from a stored standard curve and expressed as the amount of vancomycin (microgram) per mL of sample.

The purified (ammonium sulfate cut) vancomycin antibody 15-109-133 is diluted in phosphate buffer with 2.5% Bovine Serum Albumin and 10% glycerol to a concentration of 20 μg/mL which composes the S pot. The tracer pot (T pot) is a Vancomycin-DTAF tracer diluted in Tris buffer with 0.7% sodium lauryl sulfate and 0.5% lithium lauryl sulfate to a concentration of 0.275 μg/mL. Together these two components along with the pretreatment pot (P pot) yield a 96.94 mP span with intensity values ranging from 3500 to 4500 units. (Intensity values are a measure of the effect of the antibody and tracer reacting together. As either the antibody or tracer concentration is increased in the assay, the intensity value gets larger.)

Figure 11:
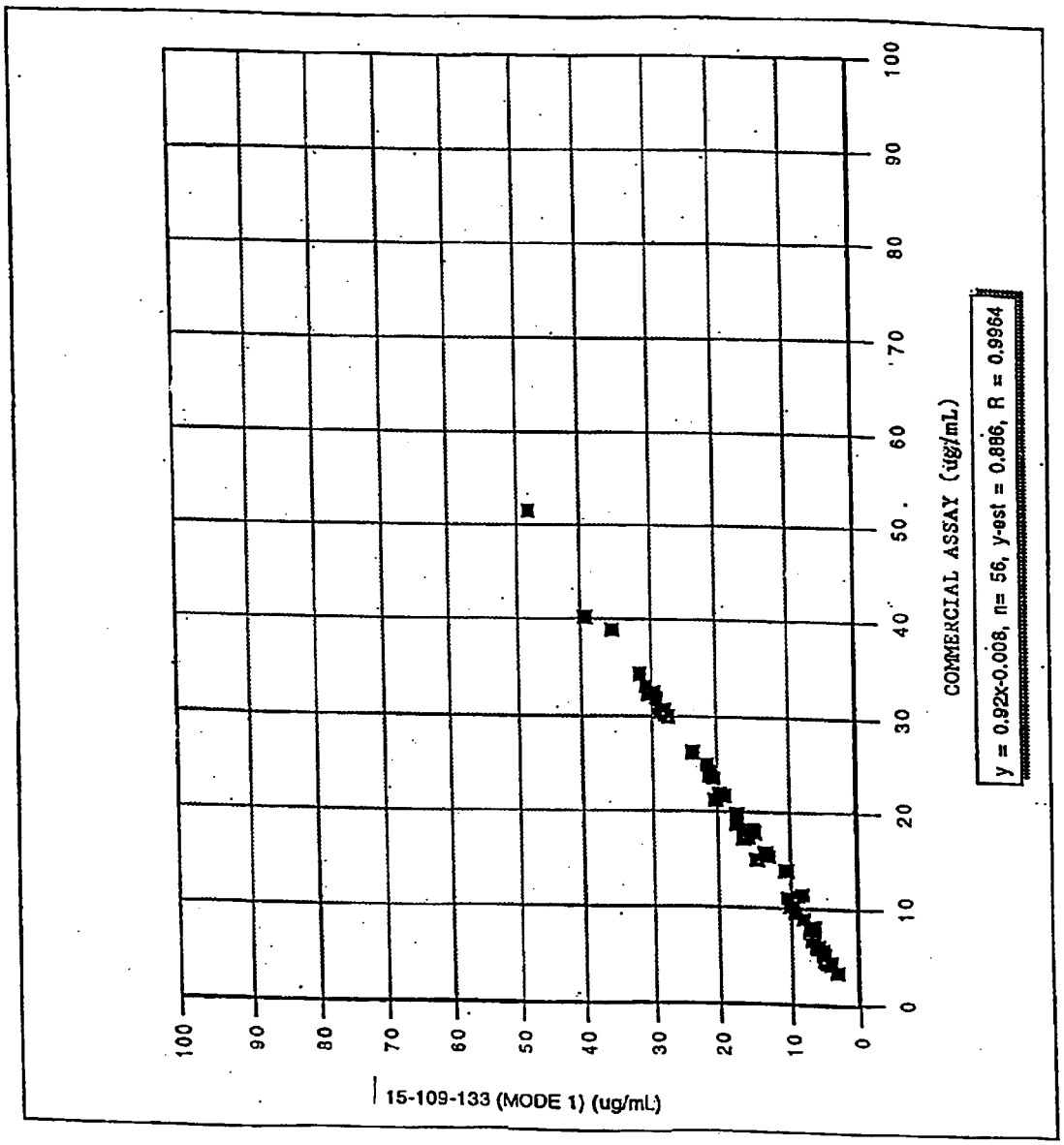
FIG. 11 shows the results of a correlation of an existing commercial assay with an assay of the present invention utilizing the most preferred antibody of the invention.
Figure 12:
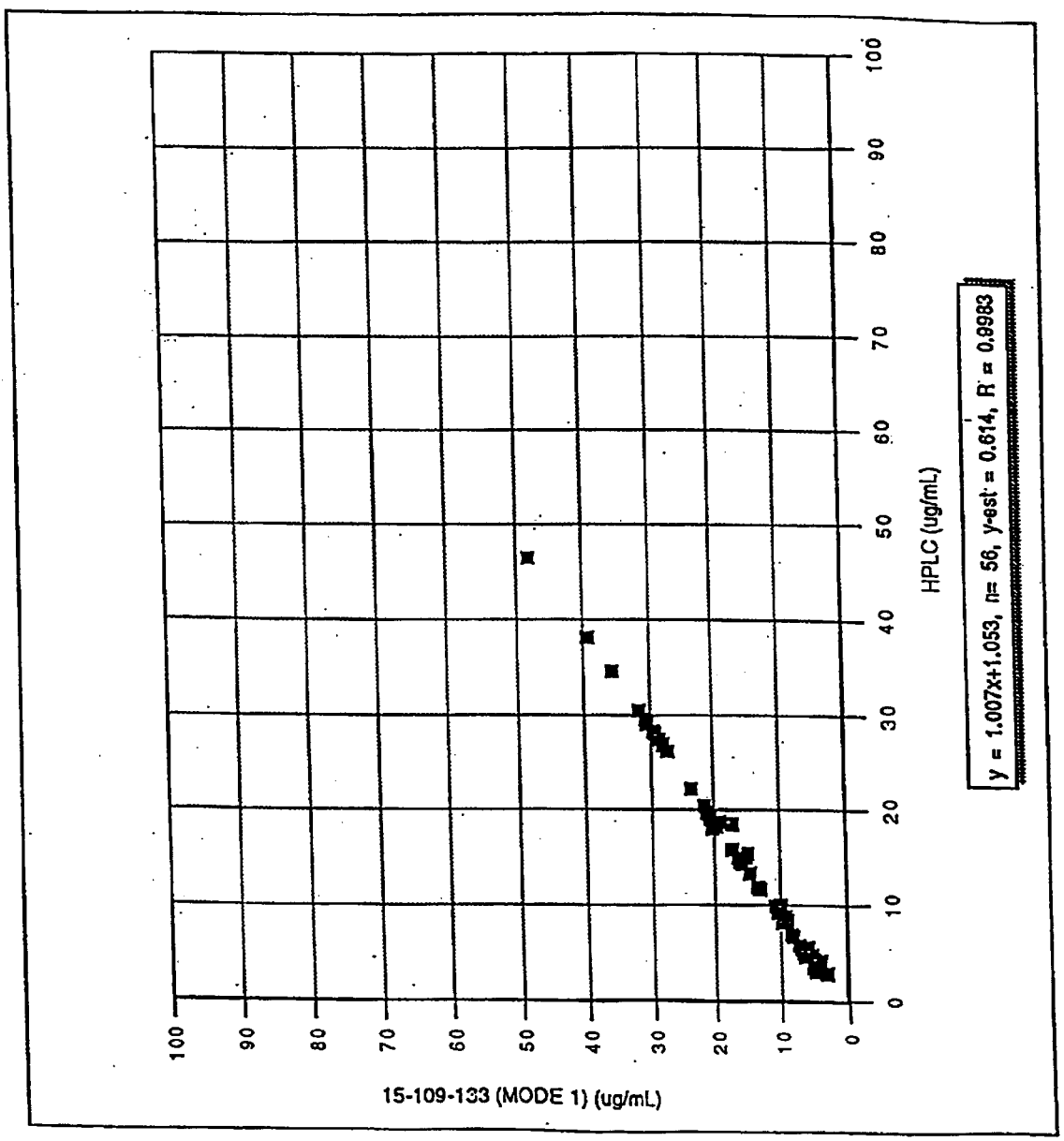
FIG. 12 shows the correlation of an assay of the present invention with HPLC.

The accuracy of the vancomycin assay of the present invention is shown by comparing it with the commercially available vancomycin assay using 56 patient samples. Both assays correlated to give an R=0.996 and y=0.92x−0.008 (FIG. 11). Furthermore, the assay of the present invention was compared to HPLC quantification. The new assay correlation against HPLC gave an R=0.998 and y=1.007+1.053 (FIG. 12), while the commercially available vancomycin assay correlated against HPLC gave an R=0.996 and y=1.088x+1.252 (Data not shown). Both the assay of the present invention and commercially available vancomycin assays have a sensitivity of less than 2.00 μg/mL and can detect between 0 and 100 μg/mL of vancomycin in a sample. Samples containing greater than 100 μg/mL of vancomycin can be automatically diluted twofold or fourfold by reducing the sample volume to 1.0 or 0.5 as instructed in the assay manual. The precision of both the assay of the present invention and the commercially available vancomycin assay are the same. All between run, within run, and total coefficient of variation (CV) are less than 6% (See Table 2).

For cross reactivities, vancomycin is tested at levels 0, 40, and 80 μg/mL with various cross reactants present at levels of 0, 1, 10, 50, and 100 μg/mL. Surprisingly, all cross reactants, including CDP-I, show less than 2% cross-reactivity with vancomycin which means all readings are below the sensitivity of the assay (2 μg/mL). In contrast, the commercially available vancomycin assay has elevated levels of CDP-I cross reactivity ranging from 39.58% to 65% with or without vancomycin present. Surprisingly, the antibody of the present invention shows no detectable cross-reactivity to CDP-I at the highest concentrations tested. These results are a significant improvement over the existing commercial assay. (Refer to Table 3 for CDP-I cross-reactivity data.)

Figure 13:
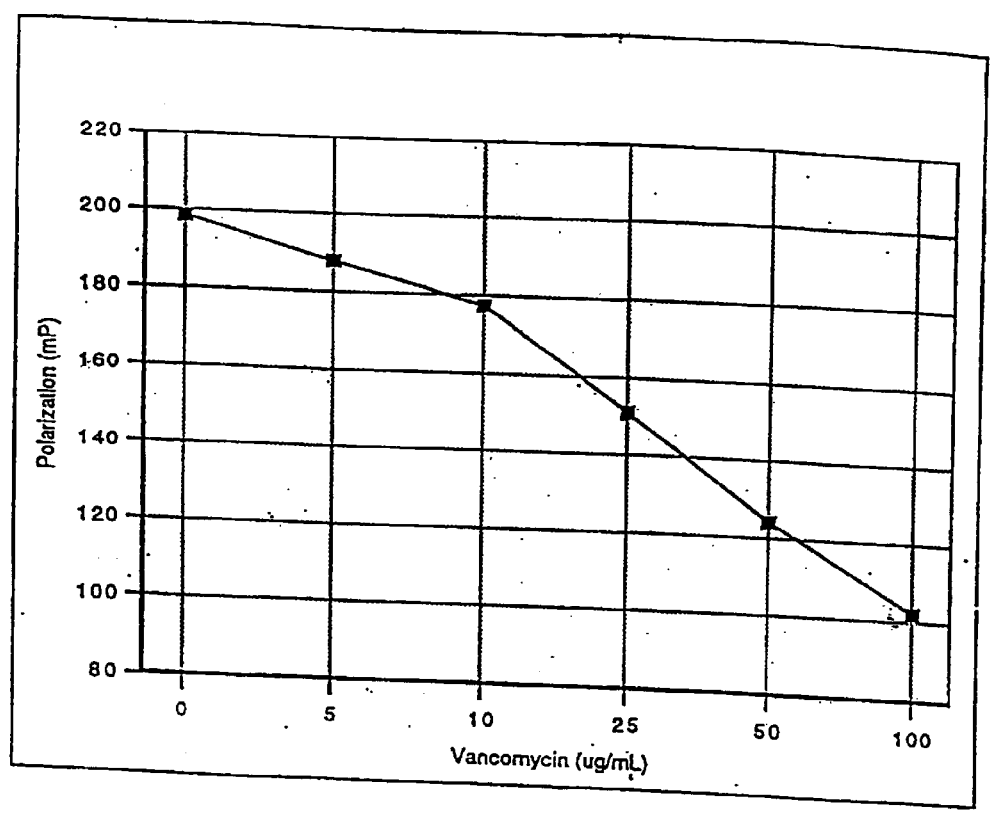
FIG. 13 shows the results of a fluorescence polarization immunoassay of the present invention.

FIG. 13 is representative of the data showing mP at 0–100 µg/mL vancomycin utilizing the method of Example 4.

The vancomycin antibody (the S pot) 15-109-592 of the present invention can be stored at 45° C. for 14 days and, it was unexpectedly discovered that the monoclonal is highly resistant to change due to freeze/thaw cycles. The monoclonal antibody can undergo three freeze/thaw cycles with minimal changes in span and intensity values. Additionally, since the antibody is a monoclonal, assay parameters such as span, cross reactivity, and stability are essentially the same form lot to lot. Furthermore, manufacturability is improved as the hybridoma may be cultured using hollow fiber tissue culture systems. The antibody also can survive at two airset fluctuations (approximately 1.5° C.) in a clinical analyzer; thus the kinetics of the assay are also stable in the analyzer environment (about 34±0.50° C.). Finally, use of a pretreatment solution (10% 5-sulfosalicylate, 0.1M Tris, 20 mM copper sulfate) allows bilirubin interference (up to 30 mg/dL) to be less than 5%, and it reduces carryover (of a 250 µg/mL vancomycin sample) to less than the sensitivity of the assay, i.e. 2%. The pretreatment solution removes the protein from any protein bound vancomycin in order to release the vancomycin for assaying.

TABLE 2

PRECISION
PRESENT INVENTION

| | | | |
|---|---|---|---|
| Target Value (ug/mL) | 7.00 | 35.00 | 75.00 |
| Mean (N = 80) | 7.13 | 35.96 | 74.48 |
| Within Run SD | 0.39 | 0.55 | 1.37 |
| Within Run % CV | 5.6% | 1.6% | 1.9% |
| Between Run SD | 0.00 | 0.60 | 0.81 |
| Between Run % CV | 0% | 1.7% | 1.1% |
| Total Precision SD | 0.42% | 1.05 | 2.39 |
| Total Precision % CV | 5.9% | 3.0% | 3.3% |

COMMERCIALLY AVAILABLE VANCOMYCIN ASSAY

| | | | |
|---|---|---|---|
| Target Value (ug/mL) | 7.00 | 35.00 | 75.00 |
| Mean (n = 80) | 6.78 | 34.39 | 72.76 |
| Within Run SD | 0.17 | 0.64 | 1.43 |
| Within Run % CV | 2.5% | 1.9% | 2.0% |
| Between Run SD | 0.20 | 0.84 | 1.15 |
| Between Run % CV | 3.0% | 2.5% | 1.6% |
| Total Precision SD | 0.40% | 1.12 | 2.53 |
| Total Precision % CV | 5.9% | 3.3% | 3.5% |

TABLE 3

CDP-I CROSS REACTIVITY
ALL VALUES ARE IN ug/mL 3a. 0 ug/mL VANCOMYCIN

| CDP-I (ug/mL) | PRESENT INVENTION VALUES | | COMMERCIAL ASSAY VALUES | |
|---|---|---|---|---|
| 1 | 0.22 | N.D. | 0.92 | N.D. |
| 2.5 | 0.15 | N.D. | 1.61 | N.D. |
| 5 | 0.26 | N.D. | 3.25 | 65% |
| 7 | LOW | N.D. | 4.54 | 64.86% |
| 10 | 0.13 | N.D. | 6.42 | 64.2% |
| 15 | LOW | N.D. | 8.87 | 59.13% |
| 20 | 0.46 | N.D. | 11.04 | 55.20% |
| 25 | 0.18 | N.D. | 12.94 | 51.76% |
| 50 | 0.67 | N.D. | 19.79 | 39.58% |

3b. 40 ug/mL VANCOMYCIN

| Sample | PRESENT INVENTION | | | COMMERCIAL ASSAY | | |
|---|---|---|---|---|---|---|
| | ug/mL | Diff/Sample-Control | % C.R. | ug/mL | Diff/Sample-control | % C.R. |
| Control | 41.06 | | | 38.94 | | |
| 1 ug/mL CDP-I | 40.86 | −0.20 | N.D. | 39.99 | 1.05 | N.D. |
| Control | 41.06 | | | 38.94 | | |
| 10 ug/mL CDP-I | 40.50 | −0.54 | N.D. | 43.74 | 4.80 | 48% |
| Control | 39.27 | | | 37.16 | | |
| 50 ug/mL CDP-I | 39.13 | −0.14 | N.D. | 55.49 | 18.33 | 36.66% |
| Control | 36.98 | | | 36.50 | | |
| 100 ug/mL CDP-I | 37.22 | 0.24 | N.D. | 67.35 | 30.85 | 30.85% |

3c. 80 ug/mL VANCOMYCIN

| Sample | PRESENT INVENTION | | | COMMERCIAL ASSAY | | |
|---|---|---|---|---|---|---|
| | ug/mL | Diff/Sample-Control | % C.R. | ug/mL | Diff/Sample-Control | % C.R. |
| Control | 79.92 | | | 79.53 | | |
| 1 ug/mL CDP-I | | −0.64 | N.D. | 78.85 | −0.68 | N.D. |
| Control | 79.92 | | | 79.53 | | |
| 10 ug/mL CDP-I | 79.49 | −0.50 | N.D. | 83.34 | 3.81 | 38.1% |
| Control | 75.24 | | | 73.21 | | |
| 50 ug/mL CDP-I | 74.41 | −0.83 | N.D. | HI (>100) | HI | HI |

TABLE 3-continued

CDP-I CROSS REACTIVITY
ALL VALUES ARE IN ug/mL

| Control | 71.48 | | | 70.00 | | |
|---|---|---|---|---|---|---|
| 100 ug/mL CDP-I | 71.22 | −0.26 | N.D. | HI (>100) | HI | HI |

N.D. = Less than sensitivity at 2.00 ug/mL vancomycin

EXAMPLE 5

Figure 15:
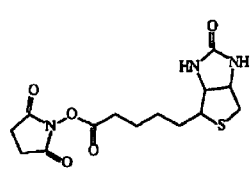
FIG. 15 shows a biotin active ester (2), a 6-carboxyfluorescein active ester (3), and an acridinium chemiluminescent label (4). These compounds are used in the various chemical schemes shown in FIG. 14 for synthesizing N-vancosaminyl derived tracers and carboxyl-HDA-derived tracers.
Figure 15:
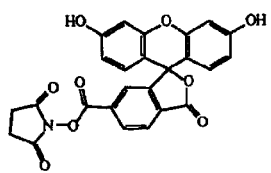
Figure 15:
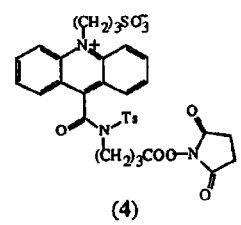

Analysis of the Structural Binding Relationships Between Vancomycin Monoclonal Antibody Fab Fragment and Vancomycin Analogs and Tracers a) Materials and Methods Protein A Affinity-Pak columns and ImmunoPure Fab preparation kits, DupH phosphate buffered saline packs, Slide-A-Lyzer 10K MWCO dialysis cassettes, the Micro BCA protein assay kit, and the Immunopure Mouse IgG F(ab')$_2$ fragment were obtained from Pierce (Rockford, Ill.). Microconcentrators were obtained from Millipore Corp. (Bedford, Mass.). Vancomycin was obtained from the Chemical and Agricultural Products Division, Abbott Laboratories (Abbott Park, Ill.). Anti-vancomycin mAb was obtained from the Abbott cell culture facility (Abbott Park, Ill.) (See Adamczyk, M., et al., *Therapeutic Drug Monitoring*, 20:191–201 (1998). (N$^\alpha$,N$^\epsilon$-diacetyl) KDADA tripeptide was obtained from Peninsula Laboratories (Belmont, Calif.). Aminocaproate-derivatized (N$^\epsilon$-acetyl) KDADA tripeptide was obtained from Research Genetics (Huntsville, Ala.). A biotin active ester, which is compound (2) shown in FIG. 15 (hereinafter referred to as "compound 2") was prepared by the method of Wilchek, as described in Wilchek, M., et al., "Biotin-containing reagents." In *Avidin-Biotin* Technology (M. Wilchek, Ed.) pp. 123–138, Academic Press, New York, herein incorporated by reference. A 6-carboxyfluorescein active ester, which is compound (3) shown in FIG. 15, (hereinafter referred to as "compound 3") was prepared by the method of Adamczyk et al. as described in Adamczyk, M., et al., *Bioconjugate Chem.*, 8:253–255 (1997), herein incorporated by reference. An acridinium chemiluminescent label, which is compound (4) shown in FIG. 15, (hereinafter referred to as "compound 4") was prepared following the general procedure described in Mattingly, P. G., *J. Biolumin. Chemilumin.* 6:107–114 (1991) and in U.S. Pat. No. 5,468,646, both herein incorporated by reference. Desvancosaminylvancomycin, which is compound (5) shown in FIG. 16, (hereinafter referred to as "compound 5") aglucovancomycin, which is compound (6) shown in FIG. 16, (hereinafter referred to as "compound 6") and N-acetylvancosaminylvancomycin, which is compound (7) shown in FIG. 16, (hereinafter referred to as "compound 7") were prepared according to the method described in Kannan, R., et al., *J. Am. Chem. Soc.*, 110:2946–2953 (1988), herein incorporated by reference. Ring-2 dechlorovancomycin, which is compound (8) shown in FIG. 16, (hereinafter referred to as compound 8") was prepared by the method described in Harris, C. M., et al., *J. Am. Chem. Soc.*, 107:6652–6658 (1985), herein incorporated by reference. Crystalline degradation product (CDP), which is compound (10) shown in FIG. 16, (hereinafter referred to as "compound 10") was prepared according to the method described in Marshall, F. J., *J. Med. Chem.* 8:18–22 (1965), herein incorporated by reference. Ring-2 dechloro CDP, which is compound (12) shown in FIG. 16, (hereinafter referred to as "compound 12") was prepared according to the method described in Harris, C. M., et al., *J. Am. Chem. Soc.*, 107:6652–6658 (1985), herein incorporated by reference. All other reagents used in synthesis were obtained from Aldrich Chemical Co. (Milwaukee, Wis.) and utilized without further purification. Synthesized compounds were purified by HPLC (Waters (Millford, Mass.) Delta Prep 3000 Preparative Chromatography system equipped with a Lambda-Max 281 UV detector, a model 740 data module, and a 40×100 mm µBONDAPAK C18 column). Analytical HPLC was performed with the same system using a 8×100 mm µBondapak C18 column. HPLC columns were eluted with a linear gradient of 5–50% CH$_3$CN in 50 mM ammonium formate (hereinafter referred to as "Solvent A") or isocratically in aqueous CH$_3$CN containing trifluoroacetic acid (v:v:v, CH$_3$CN/H$_2$O/TFA; hereinafter referred to as "Solvent B") as noted. Elution profiles were recorded at 254 nm. Electrospray ionization mass spectrometry (ESI/MS) was carried out on a Perkin-Elmer (Norwalk, Conn.) Sciex API 100 Benchtop system employing the Turbo IonSpray™ ion source. Protein was analyzed by SDS-PAGE on a BioRad Minigel system (Hercules, Calif.) utilizing 12.5% polyacrylamide gels (7 cm×10 cm×1 mm), followed by staining with Coomassie Blue. Surface plasmon resonance measurements were carried out on a BIACORE 100 (BIAcore, Inc., Piscataway, N.J.) automated system using CM-5 four-channel sensor chips. Reagents for the BIACORE instrument consisted of HBS buffer (10 mM Hepes (pH 7.4), 150 mM NaCl, 3.4 mM EDTA, and 0.05% surfactant P-20), a coupling kit containing N-hydroxysuccinimide (NHS), N-ethyl-N-(3-diethylaminopropyl)-carbodiimide (EDAC), and 1 M ethanolamine hydrochloride (pH 8.5), all from BIACORE, Inc.

b) Preparation of AglucoCDP.

Compound 10, which is CDP (See Marshall, F. J., J. Med. Chem. 8:18–22 (1965) (100 mg, 0.069 mmol), was heated on a water bath for 1 hour in 1N HCl (3 mL). The mixture was cooled to ambient temperature, and the solid was filtered off. The crude product was dissolved in saturated NaHCO$_3$, purified by preparative HPLC (Solvent A over 20 minutes; flow rate, 45 mL/minute), and lyophilized (45 mg, 57%). Analytical HPLC (Solvent A over 20 minutes; flow rate, 2 mL/minute): retention time 9.4 minutes, 99%. ESI MS m/z: 1145 (MH$^+$)

c) Procedure for the Preparation of N-Vancosaminyl Derived Vancomycin Tracers

To a solution of vancomycin (482 mg, 0.33 mmol) in dry DMF (6 mL) was added compounds 2, 3, or 4 (0.36 mmol) and triethylamine (0.91 mL, 6.6 mmol). After stirring for 24 hours at ambient temperature under N$_2$, the crude reaction mixtures were purified by preparative HPLC and lyophilized.

Compound (13), shown in FIG. 16 (hereinafter referred to as "compound 13"), was obtained from vancomycin and biotin-active ester (405 mg, 81%). Preparative HPLC (Solvent A over 20 minutes; flow rate, 45 mL/minute). Analytical HPLC (Solvent A over 15 minutes; flow rate, 2 mL/minute): retention time, 9.4 minutes, 99%. ESI/MS m/z: 1674 (MH$^+$), 1305 (MH$^+$-vancosaminyl biotin), 1143 (MH$^+$-disaccharide-biotin), 554 disaccharide+biotin+Na$^+$.

Compound (14), shown in FIG. 16 (hereinafter referred to as "compound 14"), was obtained from vancomycin and 6-carboxyfluorescein-active ester (20 mg, 11%). Preparative HPLC (Solvent B, 30:70:0.1; flow rate, 45 mL/minute).

Analytical HPLC (Solvent B, 30:70:0.1; flow rate, 2 mL/minute): retention time, 4.0 minute, 99%. ESI/MS m/z: 1809 (MH$^+$), 904 (MH$_2^{2+}$), 1305 (MH$^+$-vancosaminylfluorescein), 1143 (MH$^+$-disaccharide–fluorescein), 665 (disaccharide+fluorescein).

Compound (15), shown in FIG. 16 (hereinafter referred to as "compound 15"), was obtained from vancomycin and acridinium-active ester (409 mg, 70%). Preparative HPLC (Solvent A over 20 minutes; flow rate, 45 mL/minute). Analytical HPLC (Solvent A over 20 minutes; flow rate, 2 mL/minute): retention time, 10.4 minutes, 99%. ESI/MS m/z: 2016 (MH$^+$), 1305 (MH$^+$-vancosaminylacridinium), 1143 (MH$^+$-disaccharide–acridinium), 710 (disaccharide+acridinium).

d) Procedure for the Preparation of N-Methylleucyl Derived Vancomycin Tracers

To a solution of vancomycin (296 mg, 0.20 mmol) in DMSO (10 mL) were added biotin or 10-(3-sulfopropyl)-N-tosyl-N-(3-carboxypropyl)acridinium-9-carboxamide (0.20 mmol) and N-hydroxybenztriazole (33 mg, 0.24 mmol). Dicyclohexylcarbodiimide (206 mg, 1.0 mmol) was added, and the mixtures were stirred for 72 hours at ambient temperature under N$_2$. The crude reaction mixtures were purified by preparative HPLC and lyophilized.

Compound (16), shown in FIG. 16 (hereinafter referred to as "compound 16"), was obtained from vancomycin and biotin (136 mg, 40%). Preparative HPLC (Solvent A over 20 minutes; flow rate, 45 mL/minute). Analytical HPLC (Solvent A over 20 minutes; flow rate, 2 mL/minute): retention time, 9.4 minutes, 99%. ESI/MS m/z: 1675 (MH$^+$) 1531 (MH$^+$-vancosamine), 1372 (MH$^+$-disaccharide), 838 (MH$_2^{2+}$).

Compound (17), shown in FIG. 16 (hereinafter referred to as "compound 17"), was obtained from vancomycin and 10-(3-sulfopropyl)-N-tosyl-N-(3-carboxypropyl) acridinium-9-carboxamide (190 mg, 35%). Preparative HPLC (Solvent A was over 20 minutes; flow rate, 45 mL/minute). Analytical HPLC (Solvent A over 15 minutes; flow rate 2 mL/minute): retention time, 12.1 minutes, 99%. ESI/MS m/z: 2016 (MH$^+$), 1874 (MH$^+$-vancosamine), 1711 (MH$^+$-disaccharide), 694 (N-methylleucylacridinium).

e) Procedure for Preparation of Carboxyl Derived Vancomycin Tracers (i) Compound 9 was prepared according to the method described in Sundram, U. N., et al., J. Org. Chem. 60:1102–1103 (1995), herein incorporated by reference. To a solution of vancomycin (500 mg, 0.35 mmol) and hexanediamine hydrochloride (196 mg, 1.04 mmol) in anhydrous DMSO/DMF (v:v, 1:1, 8 mL) at 0° C. were added to HBTU (262 mg, 0.69 mmol) and diisopropylethylamine (480 μL, 2.76 mmol). After stirring for 72 hours at ambient temperature, the crude reaction mixture was purified by preparative HPLC (Solvent B, 17:83:0.0; flow rate, 40 mL/minute) and lyophilized (228 mg, 43%). Analytical HPLC (Solvent B, 17:83:0.0; flow rate, 2 mL/minute) :retention time, 7.9 minutes, 99%, ESI/MS m/z:1548 (MH$^+$).

(ii) To a solution of compound 9 (19 mg, 12 μmol) in dry DMF (0.5 mL) were added compounds 2, 3 or 4 (12 μmol), and triethylamine (2 μL, 12 μmol). After stirring for 24 hours at ambient temperature under N$_2$, the crude reaction mixtures were purified by preparative HPLC and lyophilized.

Compound (18), shown in FIG. 16 (hereinafter referred to as "compound 18"), was obtained from compound 9 and biotin active ester (9 mg, 31% based on recovered starting material. Preparative HPLC (Solvent B, 20:80:0.05; flow rate, 40 mL/minute). Analytical HPLC (Solvent B, 20:80:0.05; flow rate, 2 mL/minute): retention time, 6.1 minute, 99%. ESI/MS m/z: 1797 (M+Na$^+$), 1775 (MH$^+$), 1632 (MH$^+$-vancosamine), 1469 (MH$^+$-disaccharide).

Compound (19), shown in FIG. 16 (hereinafter referred to as "compound 19"), was obtained from compound 9 and 6-carboxyfluorescein-active ester (4 mg, 26% based on recovered starting material). Preparative HPLC (Solvent B, 27:73:0.05; flow rate, 40 mL/minute). Analytical HPLC (Solvent B, 27:73:0.05; flow rate, 2 mL/minute): retention time, 7.5 minutes, 99%. ESI/MS m/z: 1929 (M+Na$^+$), 1907 (MH$^+$), 1764 (MH$^+$-vancosamine), 1600 (MH$^+$-disaccharide).

Compound (20), shown in FIG. 16 (hereinafter referred to as "compound 20"), was obtained from compound 9 and acridinium-active ester (3 mg, 35% based on recovered starting material). Preparative HPLC (Solvent B, 27:73:0.05; flow rate, 40 mL/minute). Analytical HPLC (Solvent B, 27:73.0.05; flow rate, 2 mL/minute): retention time, 5.8 minutes, 99%. ESI/MS m/z: 2137 (M+NA$^+$), 2115 (MH$^+$), 1972 (MH$^+$-vancosamine), 1810 (MH$^+$-disaccharide).

f) Anti-vancomycin Monoclonal Antibody Preparation

Anti-vancomycin mAb which was raised against vancomycin coupled to thyroglobulin through a carboxy terminal aminobutyrate linker was purified on an Affinity-Pak Protein A column according to the manufacturer's protocol. Briefly, the cell culture containing mAb (25.4 mg) was clarified by centrifugation (3500 g, 30 minutes), filtered thorough a 0.2 μm filter, and the supernatant was applied to the Affinity-Pak Protein A column which had been equilibrated with 12 mL of IgG binding buffer. After washing with IgG binding buffer, the antibody was eluted with 6 mL of IgG elution buffer to a vial containing 1.0 mL of 1.5 M Tris buffer, pH 9.0. The purified IgG was dialyzed against PBS buffer (20 mM phosphate, 30 mM NaCl, pH 7.2) for 12 hours at 4° C. and then concentrated to approximately 10 mg/mL in an Amicon Microcon-50 microconcentration device. The mAb concentration was 12.4 mg/ML as determined by the micro-BCA protein assay as described in Smith, P. K., et al., Anal. Biochem. 150:76–85 (1985). The total recovery of the purified mAb was 18.6 mg.

g) Anti-Vancomycin Fab Fragment Preparation

The digestion of anti-vancomycin mAb was carried out with the ImmunoPure Fab preparation kit following the manufacturer's protocol. Purified anti-vancomycin mAb (approximately 12 mg) in digestion buffer (0.5 mL; 20 mM sodium phosphate, 10 mM EDTA, and 30 mM cysteine, pH 7.0) was incubated for 5 hours in 37° C. incubator-shaker with immobilized papain in digestion buffer (0.5 mL). Papain-digested anti-vancomycin mAb was then passed thorough a pre-equilibrated immobilized protein-A column (2 mL) supplied with the kit to remove undigested mAb and the Fc fragment. The protein A column was washed with an additional 13 mL of ImmunoPure binding buffer. The column flow-through and column washes containing the Fab fragment were pooled and dialyzed against PBS buffer for 12 hours at 4° C. and concentrated in a Centriprep-10 concentration device. The concentration of the anti-vancomycin Fab fragment was 2.0 mg/mL as determined by the micro-BCA method using mouse IgG (Fab')$_2$ as the standard. Purified anti-vancomycin Fab fragment was characterized by SDS-PAGE and LC/ESI mass spectrometry. The molecular weights of the heavy and light chains of the Fab fragment were 23,986 and 24,033 Da, respectively. All studies were conducted with the Fab fragment of anti-vancomycin mAb to eliminate the complexity associated with the bivalency of the monoclonal antibody.

h) Preparation of Biosensor Surfaces

Immobilization of compound 9 or the aminocaproate-derivatized (N$^\epsilon$-acetyl) KDADA tripeptide via amine coupling to the CM-5 sensor chip was performed according to the method described in Adamczyk, M., et al., Bioconjugate Chem., 9:23–32 (1998), herein incorporated by reference. Briefly, a continuous flow of HBS buffer at 10 μL/minute was initiated over the biosensor surface. The carboxymethylated dextran matrix on the sensor surface was activated by a 3.5 minute injection of a solution of 0.05 M HNS and 0.2 M EDAC. A solution of compound 9 or the aminocaproate-derivatized ($N^\epsilon$-acetyl) KDADA tripeptide (10 μM) and ethanolamine (990 μM; 1 mM total amine in HBS buffer) was then injected (7 minutes), followed by a 7 minute injection of 1.0 M ethanolamine hydrochloride to block remaining unreacted active ester groups. Blank surfaces were generated under identical conditions omitting the ligand immobilization step.

i) Solution Competition Analysis of the Vancomycin Analog/Anti-Vancomycin Fab Fragment Binding Interaction Solution competition studies were carried out on a BIAcore 2000 following the procedure described in Adamczyk, M., et al., Bioconjugate Chem., 9:23–32 (1998), herein incorporated by reference. Biosensor surfaces were regenerated after each injection with successive 1 minute pulses of 6 M, 6M, and 1.5 M guanidine hydrochloride. Initial rates of binding of anti-vancomycin Fab fragment to the biosensor surface were measured over a 15 second window beginning 20 seconds postinjection. Data was evaluated by non-linear regression analysis using the solution affinity model built into BIAevaluation 3.0 software (BIAcore, Inc).

j) Preparation of Vancomycin Analogs and Tracers

Figure 14:
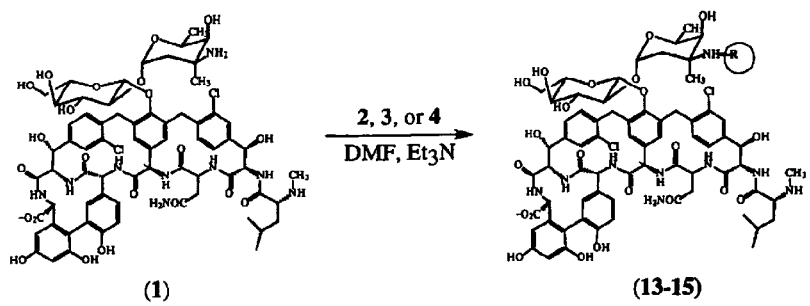
FIG. 14 shows various chemical schemes for synthesizing N-vancosaminyl derived, N-methylleucyl derived and carboxyl-HDA derived tracers.
Figure 14:
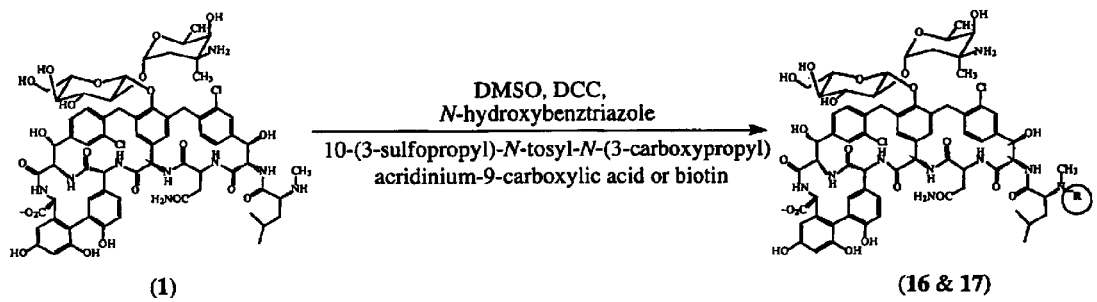
Figure 14:
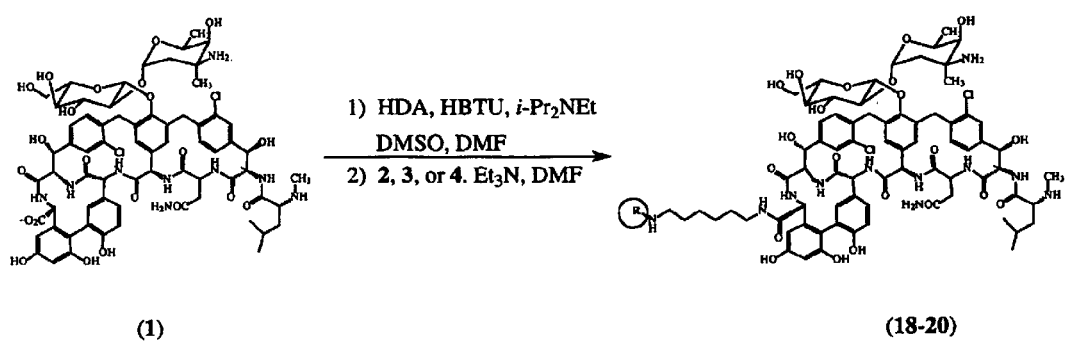

Vancomycin analogs lacking the sugars or the ring-2 chlorine were prepared as described in Kannan, R., et al., J. Am. Chem. Soc., 110:2946–2953 (1988) and Harris, C. M., et al., J. Am. Chem. Soc., 107:6652–6658 (1985). Tracer compounds 13–15, containing a derivatized N-vancosaminyl carbohydrate moiety, were prepared in 11–81% yield by coupling vancomycin with the NHS active esters of biotin (compound 2), 6-carboxyfluorescein (compound 3), or 10-(3-sulfopropyl)-N-tosyl-N-(3-carboxypropyl)acridinium-9-carboxamide (compound 4) and purification by preparative HPLC (See Scheme 1 in FIG. 14). Vancomycin tracer compounds, 16 and 17, bearing a derivatized N-methylleucyl moiety, were prepared in 40 and 35% yield, respectively, by coupling vancomycin with free biotin or acridinium acid in the presence of N,N'-dicyclohexylcarbodiimide and N-hydroxybenztriazole (See Scheme 1 in FIG. 14). Compound 9, containing an aminoalkyl linker of the free carboxyl functionality of vancomycin, was prepared by the method described in Sundram, U. N., et al., J. Org. Chem., 60:1102–1103 (1995). Coupling of compound 9 with the NHS active esters of biotin (compound 2), 6-carboxyfluorescein (compound 3), or 10-(3-sulfopropyl)-N-tosyl-N-(3-carboxypropyl) acridinium-9-carboxamide (compound 4) as above, provided mixtures of the carboxyl and N-vancosaminyl carbohydrate derivatized vancomycin tracers. Repeated purifications by preparative HPLC provided pure carboxyl modified tracer compounds 18–20 in 26–35% yield (See Scheme 1 in FIG. 14). Crystalline degradation product analogs were prepared following literature procedures or the general methodology described for the preparation of vancomycin analogs (see Marshall F. J. Structure Studies on Vancomycin, J. Med. Chem., 8:18 (1965), herein incorporated by reference). Vancomycin HCL (100 mg) was dissolved in water (2 mL) and the pH was adjusted to 4.2 with 1N NaOH. The solution was heated for 40 hours in an oil bath at an internal temperature of 60–70° C. CDP-I was recovered by filtration and washed with cold water and dried. The yield was about 60%.

k) Preparation of an Immobilized Vancomycin Biosensor Surface

Figure 17:
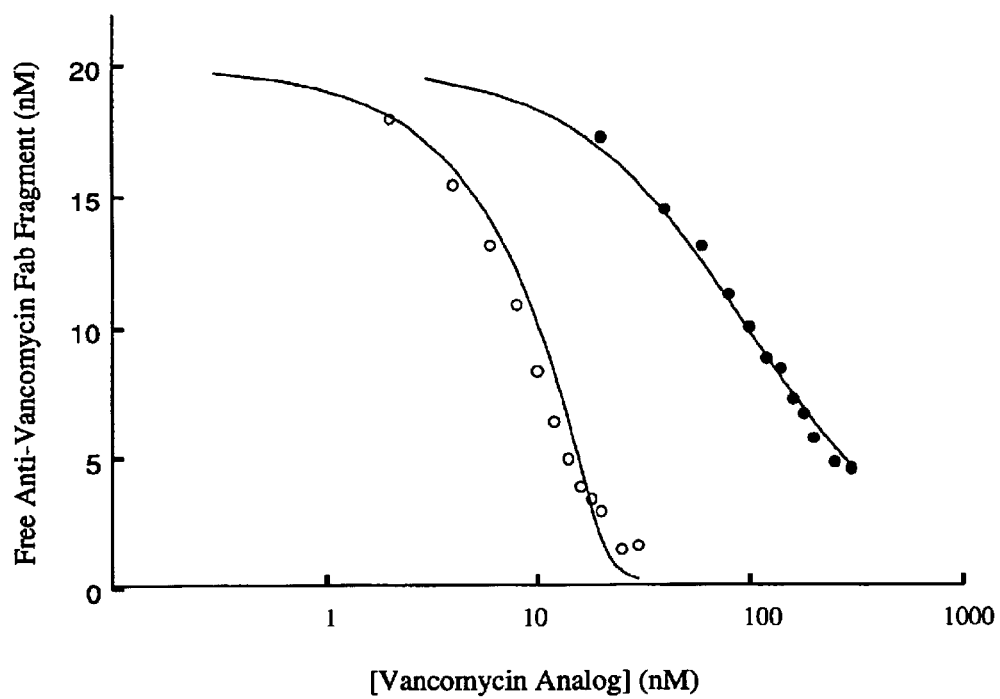
FIG. 17 shows solution competition curves for the determination of equilibrium dissociation constants for ring-2 dechlorovancomycin (represented by •) and biotinylated carboxyl-HDA vancomycin tracer (represented by ○).

Initial attempts to generate a biosensor surface involved immobilization of vancomycin to the activated carboxymethyl dextran surface of a CM-5 sensor chip through the primary amine of the vancosamine sugar moiety. Subsequent binding studies with saturating amounts of anti-vancomycin Fab fragment showed these surfaces had minimal binding capacity for the antibody fragment. In contrast, immobilization of compound 9, containing the aminoalkyl linker from the free carboxyl functionality, under identical conditions provided biosensors with relatively high binding capacity ($RU_{max}$=4000) and high affinity for anti-vancomycin Fab fragment. Additional binding studies of the anti-vancomycin Fab fragment to the immobilized aminoalkyl modified vancomycin surface demonstrated the binding to be limited by mass transfer and suitable for use in the solution binding studies described below.

l) Determination of Binding Affinities of Vancomycin Analogs and Tracers for Anti-Vancomycin Fab Fragment The binding affinities of several vancomycin analogs and tracers for anti-vancomycin Fab fragment were determined from solution competition experiments carried out on a BIAcore 2000. Initially, known concentrations of anti-vancomycin Fab fragment (0–22 nM) were injected over the aminoalkyl vancomycin biosensor surface. The initial rate of binding for each anti-vancomycin Fab fragment concentration was obtained by averaging the observed binding rate over a 145 second window beginning 20 seconds post injection. Data from the first 20 seconds of each sensorgram were omitted due to sample dispersion effects at the start of injections. A plot of initial binding rate versus concentration of anti-vancomycin Fab fragment was fit using a 4-parameter logistic (general model in BIAevaluation 3.0) providing a standard curve. Several standard curves were generated during the course of these studies and all were identical within experimental error. A fixed concentration of anti-vancomycin Fab fragment (20 nM) was then mixed with twelve concentrations of each vancomycin analog or tracer and allowed to reach equilibrium. The equilibrium mixtures were individually injected over the aminoalkyl vancomycin biosensor surface, and the concentration of free anti-vancomycin Fab fragment remaining was quantitated by determination of the initial rate of binding to the biosensor surface as described above. A plot of free anti-vancomycin Fab fragment versus total concentration of added analog or tracer provides a competition curve. FIG. 17 shows typical competition curves generated pursuant to this example. The data points represent the experimentally determined concentrations of free anti-vancomycin Fab fragment in equilibrium solutions at a given concentration of soluble analog or tracer. The curves represent the best nonlinear fit of the data using equation 1 (solution affinity model in BIAevaluation software) below:

$$Fab_f = \frac{Fab_\tau - A - K_D}{2} + \sqrt{\frac{(Fab_\tau - A - K_D)^2}{4} - A * Fab_\tau}$$

where $Fab_\tau$ is the concentration of free anti-vancomycin Fab fragment in equilibrium solutions, $Fab_\tau$ is the total concentration of anti-vancomycin Fab fragment in solution (20 nM), A is the total concentration of added vancomycin analog or tracer, and KD is the equilibrium dissociation constant for the binding of the vancomycin analog or tracer to anti-vancomycin Fab fragment in solution.

The structure-binding relationships for the interaction between vancomycin analogs and the anti-vancomycin Fab fragment, as measured by changes in the equilibrium dissociation constants (KD) is shown in Table 4, below.

TABLE 4

| Analog | Equilibrium Dissociation Constant (KD) |
|---|---|
| vancomycin (1) | ≤0.2 nM[1] |
| desvancosaminylvancomycin (5) | 587 ± 27 nM |

TABLE 4-continued

| Analog | Equilibrium Dissociation Constant (KD) |
|---|---|
| aglucovancomycin (6) | 42,000 ± 1000 nM |
| N-acetylvancosaminylvancomycin (7) | ≦0.2 nM[1] |
| Ring-2 dechlorovancomycin (8) | 87 ± 4 nM |
| carboxyl-HDA vancomycin (9) | 0.32 ± 0.04 nM |
| CDP (10) | 488 ± 34 nM |
| aglucoCDP (11) | ≧50,000 nM[2] |
| Ring-2 dechloroCDP (12) | 6,000 ± 100 nM |

[1]KD was too small to be reliably measured by solution affinity experiments.
[2]KD was too large to be reliably measured by solution affinity experiments.

Table 4 shows that vancomycin and the N-acetylvancomsaminyl derivatized analog (compound 7) bind exceedingly tight with KD values being outside the range for which the BIAcore instrument can accurately provide values from solution competition studies. Incorporation of the aminoalkyl linker on the free carboxyl functionality of vancomycin, providing compound 9, which was used for preparation of the immobilized vancomycin biosensor surface, have minimal effect on the anti-vancomycin Fab fragment recognition in solution. Removal of the ring-2 chlorine atom from vancomycin results in a significant loss in binding recognition by the antibody fragment (see the results for compound 8 in the Table 4, above). Cleavage of one or both of the carbohydrate rings from vancomycin by acid hydrolysis which provides compounds 5 and 6, respectively, results in a further sequential loss in binding recognition by the antibody fragment with the loss of each monosaccharide. Anti-vancomycin Fab fragment binding interactions with vancomycin degradation products were extremely weak relative to the native antibiotic binding interaction. Crystalline degradation product (compound 10) binds with a KD of 488±34 nM. Removal of the chlorine atom from the 2-position results in a significant loss in binding recognition by the anti-vancomycin Fab fragment and, complete hydrolysis of the carbohydrate rings, providing compound 11, results in a binding interaction with the anti-vancomycin Fab fragment too weak to be determined by the solution competition studies.

The structure-binding relationships for the binding interaction between vancomycin tracers and the anti-vancomycin Fab fragment, as measured by changes in the equilibrium dissociation constants (KD), are summarized in Table 5.

TABLE 5

| | Derivation Site | | |
|---|---|---|---|
| Derivative | N-Vancosaminyl | N-Methylleucyl | Carboxyl-HDA |
| biotin | 584 ± 19 nM | ≦0.2 nM[1] | 0.17 ± 0.04 nM |
| fluorescein | 76 ± 3 nM | (–)[3] | 206 ± 6 nM |
| acridinium | 1200 ± 100 nM | 25 ± 0.7 nM | 26 ± 0.9 nM |

Figure 18:
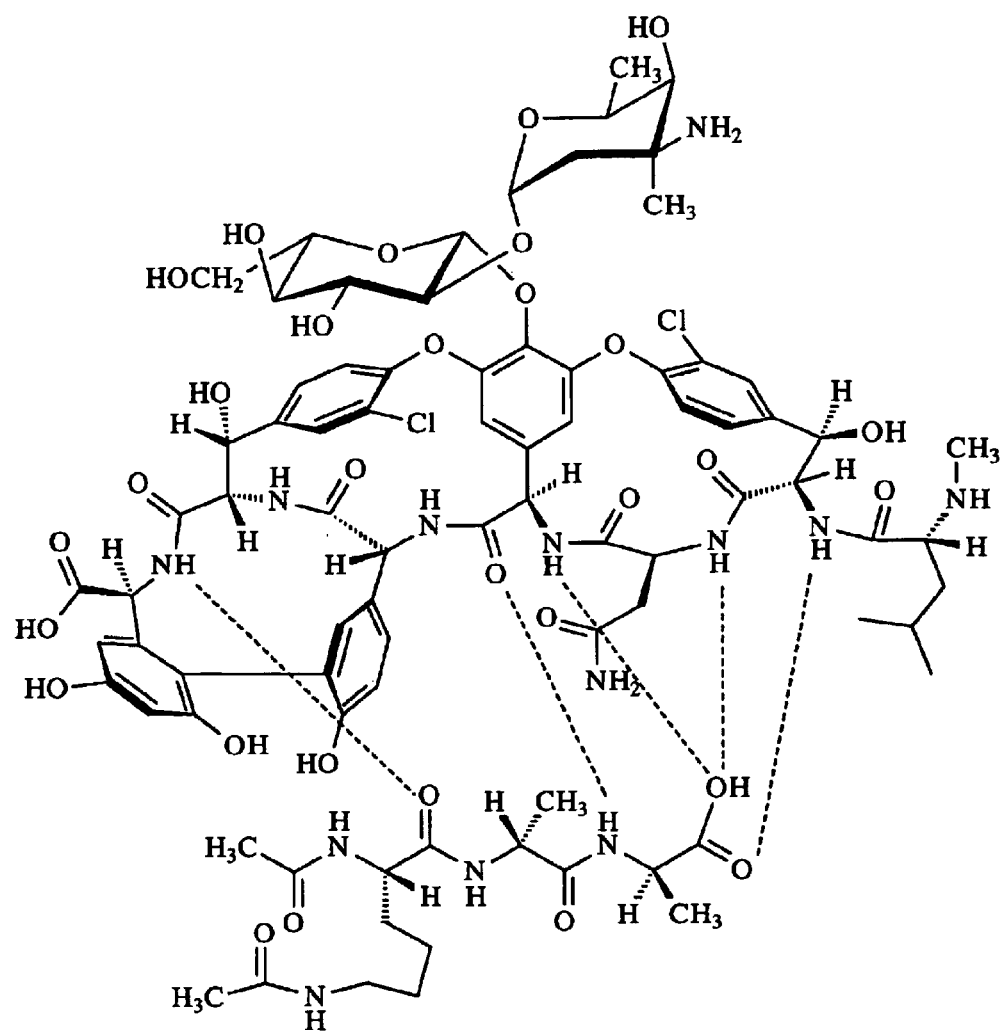
FIG. 18 shows a model of the binding interaction between vancomycin and a cell wall peptide analog, ($N^\alpha N^\epsilon$-diacetyl) KAA. Dashed lines represent hydrogen bonds.
Figure 19:
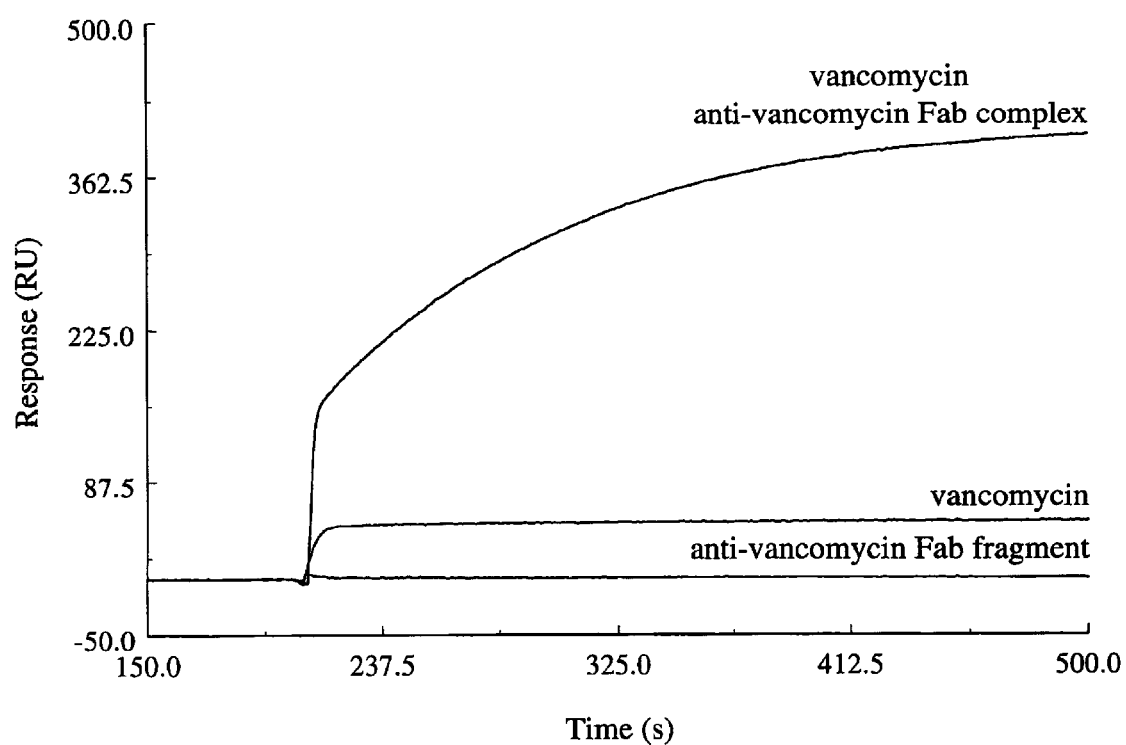
FIG. 19 shows the binding of vancomycin, anti-vancomycin Fab fragment, and vancomycin/antivancomycin Fab fragment complex to aminocaproate-derivatized ($N^\epsilon$-acetyl)KAA tripeptide biosensor surface.

[1]KD was too small to be reliably measured by solution affinity experiments.
[2]Not determined Table 5 shows that the binding interactions varied depending on the label contained on the tracer. However, N-methylleucyl-(compounds 16 and 17) and carboxyl-HDA-derived tracers (compounds 18–20) containing the same label bind the antibody fragment with similar affinities. In contrast, N-vancosaminyl derived tracers (compounds 13–15) containing the equivalent label bind the antibody fragment substantially weaker.

m) Evaluation of a Vancomycin/KDADA Tripeptide Binding Interaction on Anti-vancomycin Fab Fragment Recognition To further evaluate the topology of vancomycin that is critical for anti-vancomycin Fab fragment recognition, the role of residues located in the peptide binding pocket of the antibiotic was investigated (See FIG. 18). For these studies, an ($N^\epsilon$-acetyl) KDADA tripeptide containing an aminocaproate linker from the amino terminus was immobilized via amine coupling to an activated carboxymethyl dextran surface of a CM-5 sensor chip. Vancomycin (0.5 μM) binds to this surface (See FIG. 19). However, since the mass of the antibiotic is small, the instrumental response is relatively small (approximately 50 Rus at equilibrium). In contrast, injection of a vancomycin (0.5 μM)/anti-vancomycin Fab fragment (1 μM) complex, in which ≧99% of the vancomycin is bound by the antibody fragment, results in approximately 10-fold increase in response due to the increased mass of the complex (see FIG. 19). Anti-vancomycin Fab fragment alone has no affinity for the immobilized tripeptide surface (FIG. 19). To further verify that the peptide and antibody binding pockets of vancomycin were mutually exclusive, the vancomycin/anti-vancomycin Fab fragment solution binding interaction was reinvestigated under the conditions described above in the presence of ($N^a,N^\epsilon$-diacetyl) KDADA tripeptide (500 μM). The KD value obtained for the vancomycin/anti-vancomycin Fab fragment binding interaction in solution in the presence of ($N^a,N^\epsilon$-diacetyl)KDADA tripeptide was identical to the value obtained in the absence of the tripeptide (≦0.2 nM).

We claim:

1. A method for the quantification of vancomycin in a test sample, the method comprising the steps of:

(a) contacting the test sample with
 (i) an antibody reagent comprising antibodies secreted by a hybridoma cell line designated as ATCC HB 11834, and
 (ii) a labeled reagent of the formula:

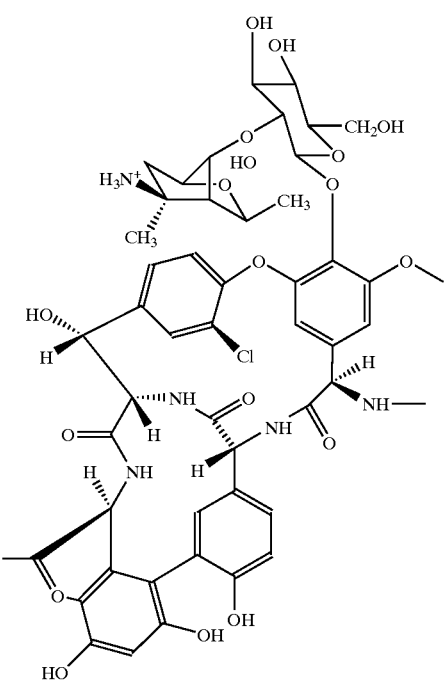

-continued

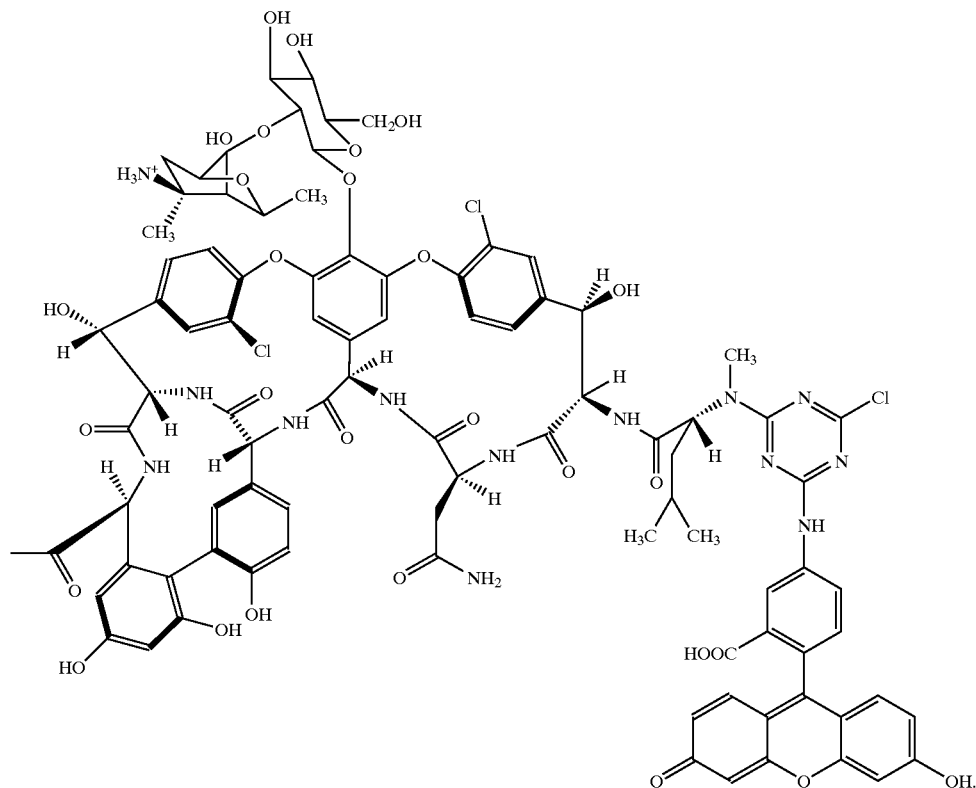

wherein Q is a detectable moiety and X is from 0 to 50 carbon and heteroatoms, including not more than ten heteroatoms, arranged as a straight or branched chain or cyclic moiety, saturated or unsaturated, with the provisos that not more than two heteroatoms may be directly linked in sequence, that the sequence cannot contain —O—O linkages, the cyclic moieties contain 6 or fewer members, and that branching may occur only on carbon atoms, to form a reaction solution; and (b) measuring the amount of the labeled reagent in the reaction solution which either is or is not bound with the antibody as a function of the amount of vancomycin in the test sample.

2. The method of claim 1 wherein the detectable moiety is selected from the group consisting of enzymes, chromophores, fluorescent molecules, chemiluminescent molecules, phosphorescent molecules, and luminescent molecules.

3. The method of claim 1, wherein the immunoassay method is a fluorescent polarization immunoassay wherein the detectable moiety of the labeled reagent is a fluorescent molecule.

4. The method of claim 3, wherein the measurement in step (b) is made by (a) passing a plane of polarized light through the reaction solution to obtain a fluorescence polarization response and (b) detecting the fluorescence polarization response of the reaction solution as a measure of the amount of vancomycin an the test sample.

5. The method of claim 4, wherein the fluorescent molecule is selected from the group consisting of aminomethylfluorescein, amino-fluorescein, 5-carboxyfluorescein, 6-carboxyfluorescein, thioureafluorescein, and dichlorotriazinyl-amninofluorescein.

6. The method of claim 5, wherein the labeled reagent is sample, wherein said antibodies are secreted by a hybridoma cell line designated ATCC HB 11834;

7. An antibody secreted by a hybridoma cell line designated ATCC HB 11834.

8. A test kit for the quantification of vancomycin in a test sample, the test kit comprising:

(a) an antibody reagent comprising antibodies which are capable of specifically binding vancomycin in a test sample, wherein said antibodies are secreted by a hybridoma cell line designated ATCC HB 11834;

(b) a labeled reagent which is capable of displacing the binding of the antibody to the vancomycin; and (c) a stable calibrator comprising an aqueous solution containing a polypeptide stabilized vancomycin molecule wherein said polypeptide does not interfere with the binding of an antibody to the vancomycin molecule.

9. The kit of claim 8 wherein the labeled reagent is of the formula:

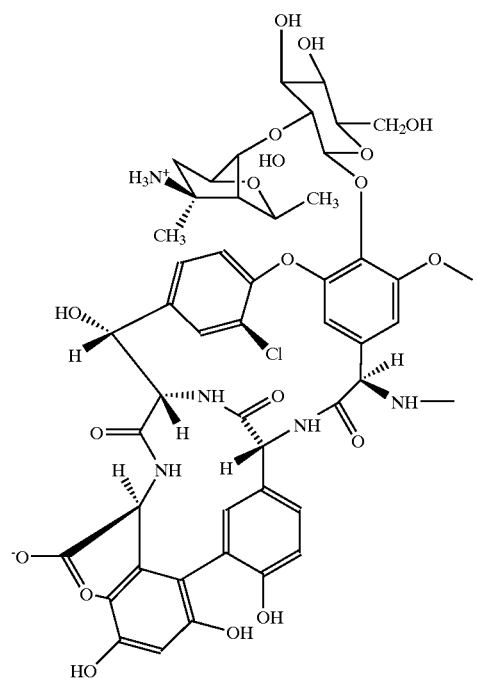

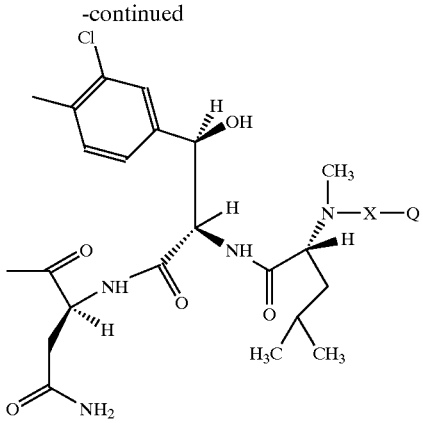

wherein Q is a detectable moiety and X is of from 0 to 50 carbon and heteroatoms, including not more than ten heteroatoms, arranged as a straight or branched chain or cyclic moiety, saturated or unsaturated, with the provisos that not more than two heteroatoms may be directly linked in sequence, that the sequence cannot contain —O—O linkages, that cyclic moieties contain 6 or fewer members, and that branching may occur only on carbon atoms.

* * * * *